US012016520B2

(12) United States Patent
Takahashi et al.

(10) Patent No.: US 12,016,520 B2
(45) Date of Patent: Jun. 25, 2024

(54) FLEXIBLE TUBE INSERTION APPARATUS, INSERTION CONTROL APPARATUS, AND INSERTION CONTROL METHOD

(71) Applicant: OLYMPUS CORPORATION, Tokyo (JP)

(72) Inventors: Takeshi Takahashi, Hachioji (JP); Ryo Tezuka, Hachioji (JP); Tomohiro Kitanaka, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 671 days.

(21) Appl. No.: 16/992,599

(22) Filed: Aug. 13, 2020

(65) Prior Publication Data

US 2020/0367724 A1    Nov. 26, 2020

Related U.S. Application Data

(63) Continuation of application No. PCT/JP2018/005762, filed on Feb. 19, 2018.

(51) Int. Cl.
*A61B 1/00* (2006.01)
*A61B 1/005* (2006.01)
(Continued)

(52) U.S. Cl.
CPC ...... *A61B 1/00006* (2013.01); *A61B 1/00078* (2013.01); *A61B 1/00158* (2013.01);
(Continued)

(58) Field of Classification Search
CPC .............. A61B 1/0051; A61B 1/00078; A61B 1/00158; A61B 1/31; G06V 10/255; G06K 9/00536
See application file for complete search history.

(56) References Cited

U.S. PATENT DOCUMENTS 6,868,195 B2 * 3/2005 Fujita ..................... A61B 1/009
356/73.1
10,349,819 B2 * 7/2019 Ikeda ................. A61B 1/00006

FOREIGN PATENT DOCUMENTS

JP        2007-054401 A    3/2007
WO    WO 2016/151846 A1    9/2016
(Continued)

OTHER PUBLICATIONS

WO-2016151845-A1 English Translation (Year: 2016).*
(Continued)

*Primary Examiner* — Ryan N Henderson
*Assistant Examiner* — Megan Elizabeth Monahan
(74) *Attorney, Agent, or Firm* — Scully, Scott, Murphy & Presser, P.C.

(57) ABSTRACT

A flexible tube insertion apparatus includes a flexible tube to be inserted into a tract, a shape calculation system configured to calculate a shape of the flexible tube, and a bend detection unit configured to detect formation of first and second bend portions in the flexible tube, based on information of the calculated shape of the flexible tube. The apparatus also includes a positional relationship calculation unit configured to calculate a three-dimensional positional relationship expressed by a crossing angle between first and second imaginary planes respectively passing through the first and second bend portions, and a stiffness control system configured to control a stiffness of the flexible tube, based on the three-dimensional positional relationship.

12 Claims, 20 Drawing Sheets

(51) Int. Cl.
  *G06V 10/10* (2022.01)
  *G06V 10/764* (2022.01)
  *G06V 20/64* (2022.01)
  *A61B 1/31* (2006.01)
(52) U.S. Cl.
  CPC ............ *A61B 1/0051* (2013.01); *G06V 10/17* (2022.01); *G06V 10/764* (2022.01); *G06V 20/64* (2022.01); *A61B 1/31* (2013.01); *G06F 2218/12* (2023.01)

(56) References Cited

FOREIGN PATENT DOCUMENTS

| WO | WO-2016151846 A1 * | 9/2016 | ......... A61B 1/00078 |
| WO | WO 2016/199305 A1 | 12/2016 | |
| WO | WO 2017/109988 A1 | 6/2017 | |
| WO | WO 2017/109989 A1 | 6/2017 | |
| WO | WO 2017/212615 A1 | 12/2017 | |

OTHER PUBLICATIONS

International Search Report dated May 22, 2018 issued in PCT/JP2018/005762.
English translation of International Preliminary Report on Patentability dated Sep. 3, 2020 together with the Written Opinion issued in International Application No. PCT/JP2018/005762.

* cited by examiner

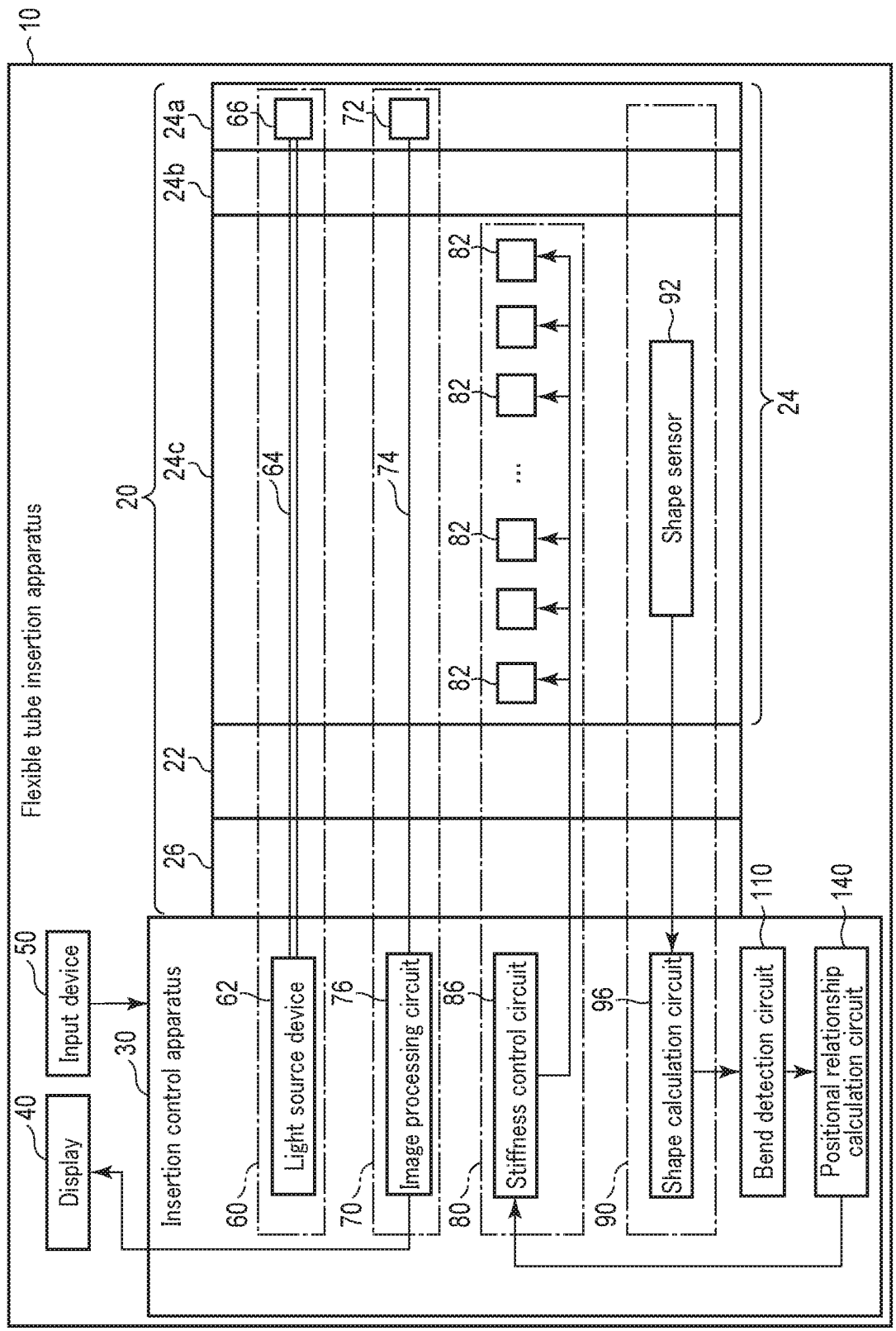
F I G. 2

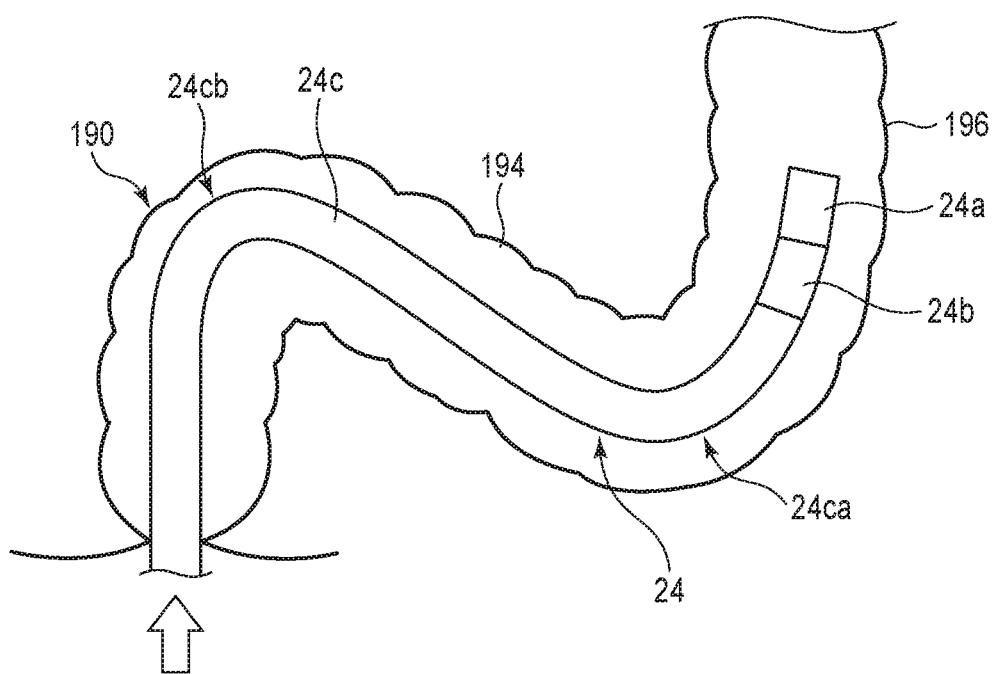
F I G. 12

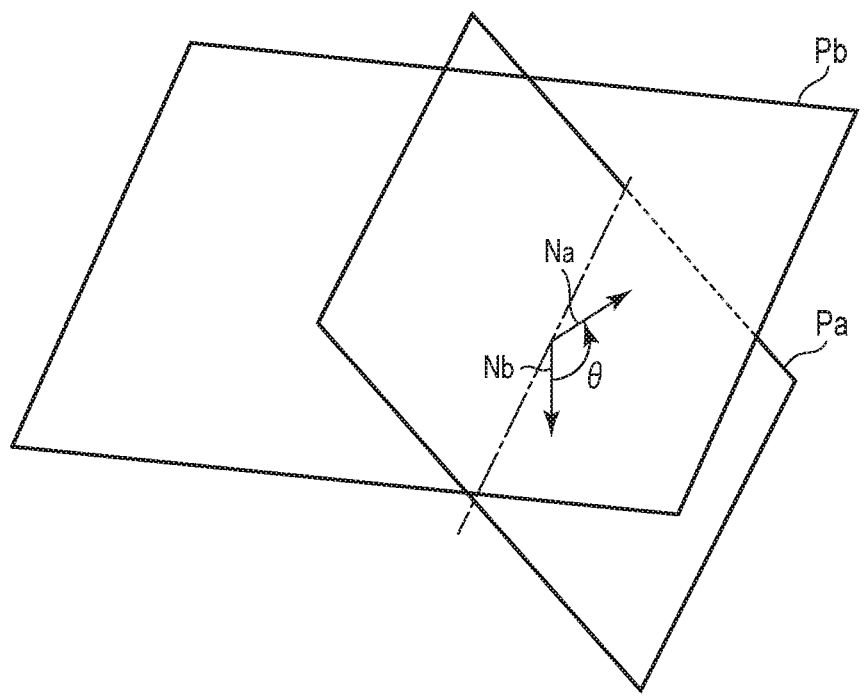
F I G. 14
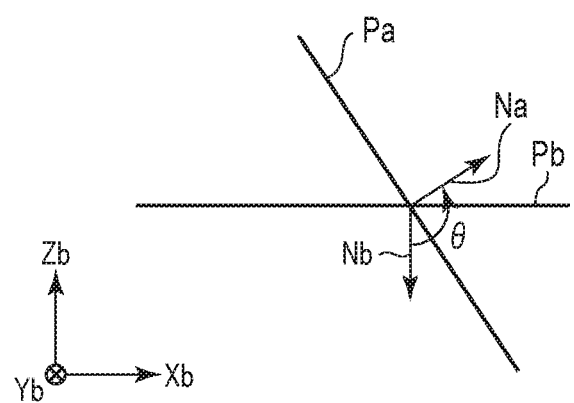
F I G. 15

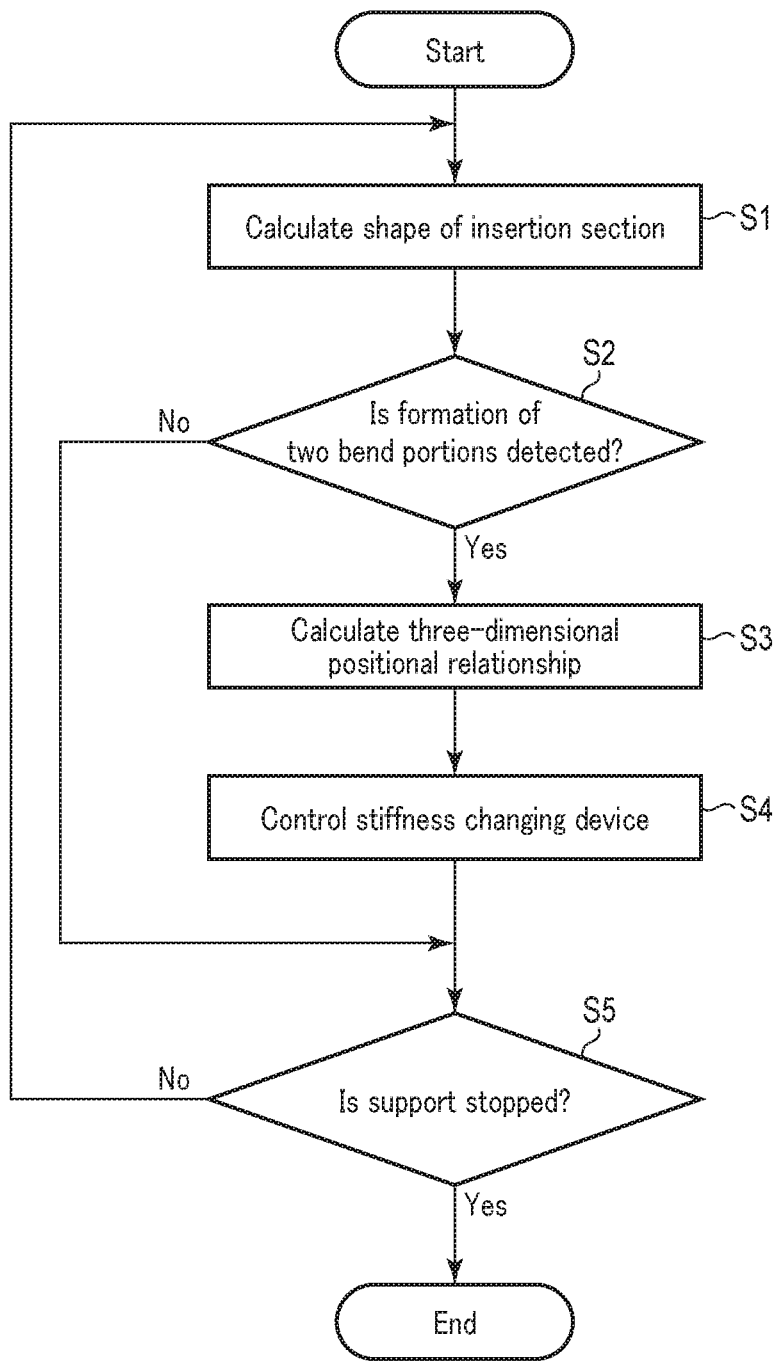
F I G. 20

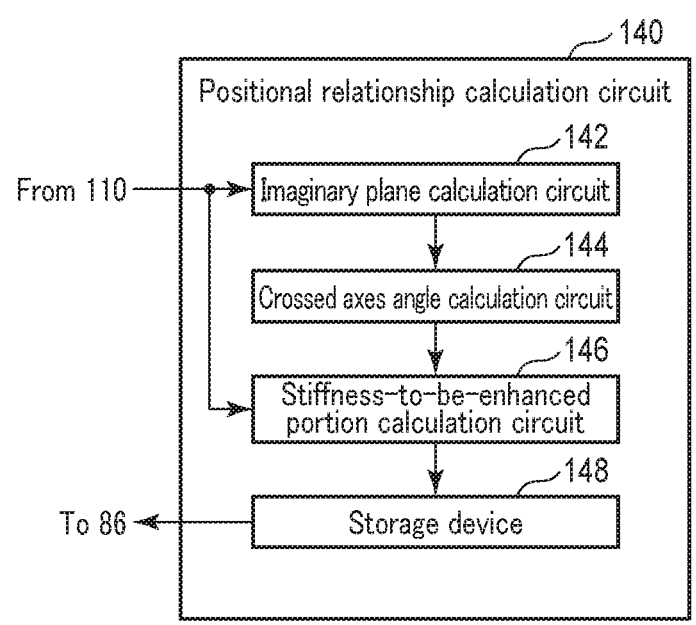
F I G. 21

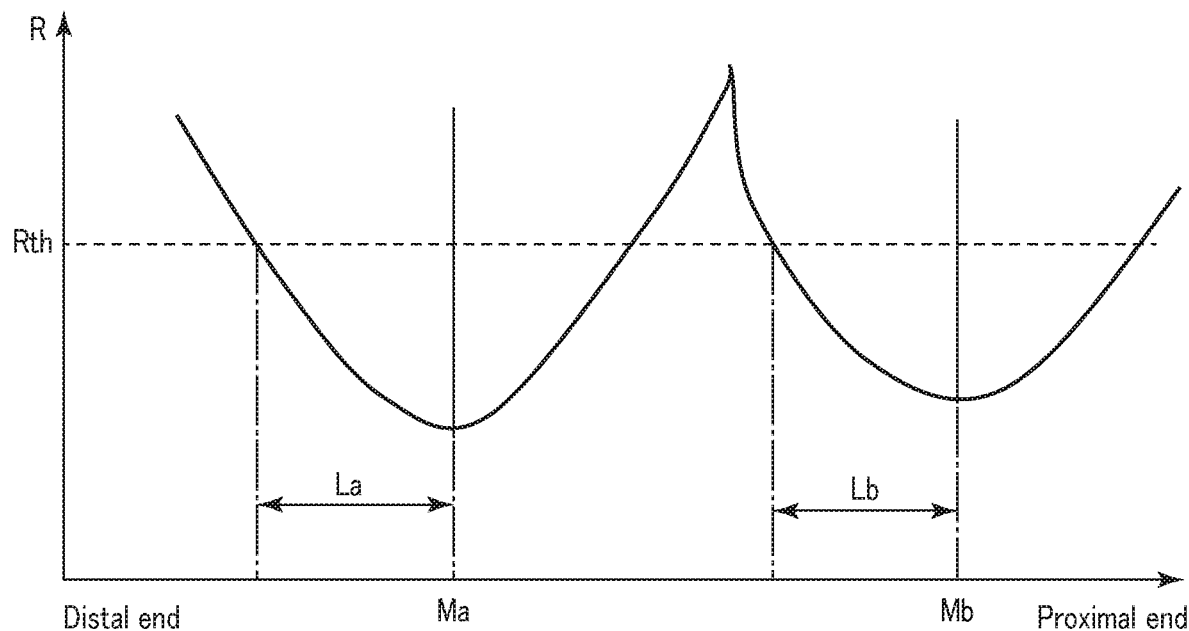
F I G. 22
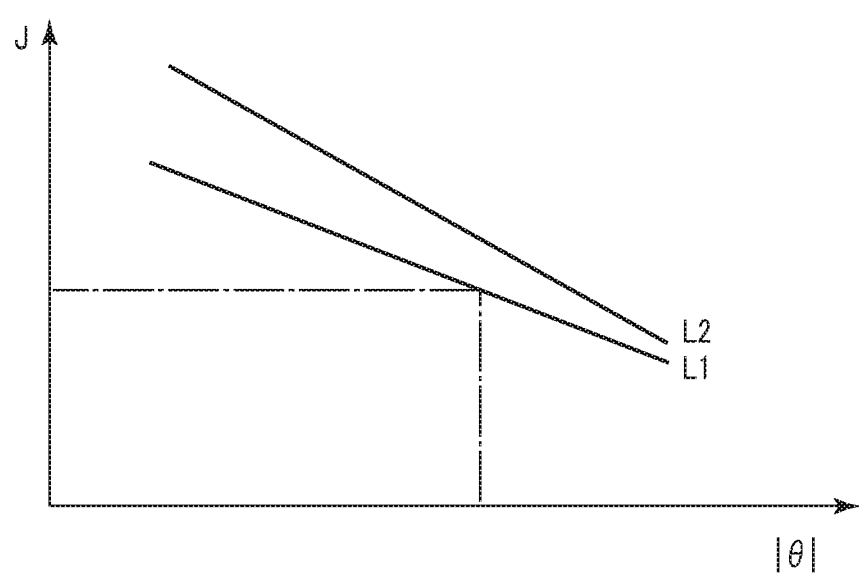
F I G. 23

[A pattern]

[B pattern]

[C pattern]

FLEXIBLE TUBE INSERTION APPARATUS, INSERTION CONTROL APPARATUS, AND INSERTION CONTROL METHOD

CROSS-REFERENCE TO RELATED APPLICATIONS

This application is a Continuation Application of PCT Application No. PCT/JP2018/005762, filed Feb. 19, 2018, the entire contents of which are incorporated herein by reference.

BACKGROUND OF THE INVENTION

1. Field of the Invention

The present invention relates to a flexible tube insertion apparatus including a flexible tube to be inserted into a tract of a target, an insertion control apparatus of the flexible tube, and an insertion control method of the flexible tube.

2. Description of the Related Art

As one of flexible tube insertion apparatuses, there is known an endoscope apparatus including an endoscope.

The endoscope includes a soft, elongated insertion section to be inserted into a tract of a target. The insertion section includes an imaging element in a distal portion thereof. The insertion section also includes a soft tube composed of a flexible tube. Further, as one of endoscopes, there is known a colonoscope designed to be inserted into the large intestine.

The large intestine is generally classified into the rectum, colon, and cecum from the anus side, and the colon is further classified into the sigmoid colon, descending colon, transverse colon, and ascending colon from the rectum side. In general, the sigmoid colon and the transverse colon are not fixed in the abdominal part and easily move. If the insertion section of the endoscope is inserted into such an intestinal tract, the insertion section advances in the intestinal tract while bending along the intestinal wall.

There is a case in which in the insertion section inserted in the large intestine, the soft tube exhibits a loop shape, in particular, in the sigmoid colon. When the insertion section is further advanced deeper, there is a case in which an operator advances the insertion section to a deep part of the descending colon while forming a loop in the soft tube.

International Publication No. 2016/151846 discloses, as a technology for enhancing the insertability of an insertion section in which a loop is formed, a technique of enhancing the stiffness of a distal portion of a bend part of the loop.

International Publication No. 2016/199305 discloses, as another technology for enhancing the insertability of the insertion section in which a loop is formed, a technique of changing the stiffness of various portions of the insertion section, based on insertion patterns in the past, and controlling the stiffness of various portions in accordance with the change of the shape of a tract due to the insertion of the insertion section.

BRIEF SUMMARY OF THE INVENTION

A flexible tube insertion apparatus according to the present invention includes: a flexible tube to be inserted into a tract of a target; a shape calculation system configured to calculate a shape of the flexible tube; a bend detection unit configured to detect formation of a first bend portion and a second bend portion in the flexible tube, based on information of the shape of the flexible tube calculated by the shape calculation system, the second bend portion being located on a proximal side of the flexible tube with respect to the first bend portion; a positional relationship calculation unit configured to calculate a three-dimensional positional relationship that is capable of being expressed by a crossing angle between a first imaginary plane passing through the first bend portion and a second imaginary plane passing through the second bend portion; and a stiffness control system configured to control a stiffness of the flexible tube, based on the three-dimensional positional relationship.

An insertion control apparatus according to the present invention includes: a shape calculation system configured to calculate a shape of a flexible tube to be inserted into a tract of a target; a bend detection unit configured to detect formation of a first bend portion and a second bend portion in the flexible tube, based on information of the shape of the flexible tube calculated by the shape calculation system, the second bend portion being located on a proximal side of the flexible tube with respect to the first bend portion; a positional relationship calculation unit configured to calculate a three-dimensional positional relationship that is capable of being expressed by a crossing angle between a first imaginary plane passing through the first bend portion and a second imaginary plane passing through the second bend portion; and a stiffness control system configured to control a stiffness of the flexible tube, based on the three-dimensional positional relationship.

An insertion control method according to the present invention includes: calculating a shape of a flexible tube to be inserted into a tract of a target; detecting formation of a first bend portion and a second bend portion in the flexible tube, based on information of the shape of the flexible tube, the second bend portion being located on a proximal side of the flexible tube with respect to the first bend portion; calculating a three-dimensional positional relationship that is capable of being expressed by a crossing angle between a first imaginary plane passing through the first bend portion and a second imaginary plane passing through the second bend portion; and controlling a stiffness of the flexible tube, based on the three-dimensional positional relationship.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 shows functional blocks of the flexible tube insertion apparatus shown in FIG. 1.

FIG. 12 shows the insertion section inserted in the large intestine.

FIG. 14 is a perspective view of a distal imaginary plane and a proximal imaginary plane.

FIG. 15 is a side view of the distal imaginary plane and the proximal imaginary plane.

FIG. 20 shows a flowchart of a process in an insertion support operation of the insertion section in the flexible tube insertion apparatus shown in FIG. 2.

FIG. 21 shows a configuration example of a positional relationship calculation circuit shown in FIG. 2.

FIG. 22 is a graph showing a radius of curvature of various portions of the insertion section inserted in the large intestine.

FIG. 23 is a graph showing a relationship between a magnitude of a crossing angle of two imaginary planes, and a control target value of the stiffness changing device.

DETAILED DESCRIPTION OF THE INVENTION

Here, as regards a flexible tube insertion apparatus according to the present embodiment, an example in which the flexible tube insertion apparatus is applied to a medical endoscope will be described. The medical endoscope may be, for example, an upper gastrointestinal endoscope, a colonoscope, an ultrasonic endoscope, a cystoscope, or a pyeloscope. The flexible tube insertion apparatus according to the present embodiment is not limited to the medical endoscope, and is generally applicable to a device configured to operate a flexible tube and to perform operations such as insertion and treatment. Examples of this device include a catheter and a medical manipulator. Further, the flexible tube insertion apparatus according to the present embodiment may be an industrial endoscope.

[Flexible Tube Insertion Apparatus 10]

Figure 1:
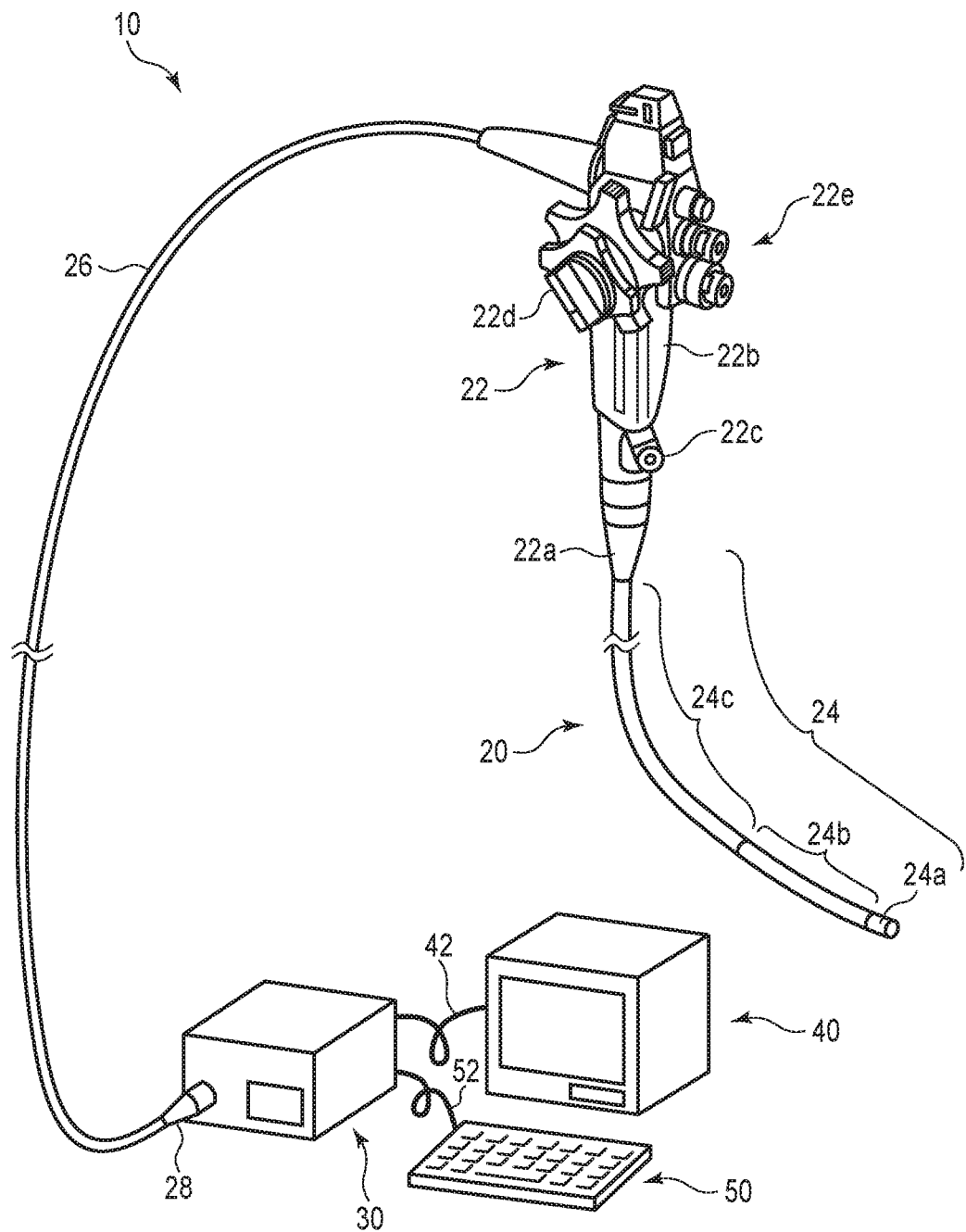
FIG. 1 shows a flexible tube insertion apparatus according to an embodiment.

FIG. 1 shows a flexible tube insertion apparatus 10 according to the present embodiment. The flexible tube insertion apparatus 10 includes an endoscope 20; an insertion control apparatus 30 to which the endoscope 20 is connected; a display 40 that is connected to the insertion control apparatus 30; and an input device 50 that is connected to the insertion control apparatus 30.

The endoscope 20 includes an elongated insertion section 24 to be inserted into a tract of an observation target; a control section 22 coupled to a proximal portion of the insertion section 24; and a universal cord 26 extending from the control section 22.

The insertion section 24 includes a hard distal section 24a that is composed to be hard; an active bendable section 24b coupled to the proximal side of the hard distal section 24a; and a soft tube 24c that is a flexible tube coupled to the proximal side of the active bendable section 24b. The hard distal section 24a includes, for example, an illumination light emission unit configured to emit illumination light that illuminates an observation target; and an imaging element configured to image the observation target. The active bendable section 24b can be bent in a desired direction by operating the control section 22. Specifically, the active bendable section 24b is configured to be actively bendable. The soft tube 24c is configured to be passively bendable. For example, the soft tube 24c, when inserted into a tract of the observation target, is bent in accordance with the shape of the tract.

The control section 22 includes a protection hood portion 22a coupled to the proximal side of the soft tube 24c; and a gripper 22b coupled to the proximal side of the protection hood portion 22a. The protection hood portion 22a is provided with a treatment instrument insertion hole 22c communicating with an insertion channel extending in the insertion section 24. The gripper 22b includes a bending operation dial 22d for bend-operating the active bendable section 24b; and switches 22e for performing air feed, water feed, suction, imaging, etc.

The endoscope 20 is connected to the insertion control apparatus 30 by the universal cord 26. The universal cord 26 includes a connection portion 28 that is detachably attached to the insertion control apparatus 30. The connection portion 28 functions as an interface of data that is transmitted and received between the endoscope 20 and the insertion control apparatus 30.

The display 40 is a device configured to display various kinds of information, such as an observation image by the endoscope 20. The display 40 is connected to the insertion control apparatus 30 through a cable 42. The display 40 may be composed of, for example, a liquid crystal display, although the display 40 is not limited to this.

The input device 50 is a general device for input, such as a keyboard. The input device 50 is connected to the insertion control apparatus 30 through a cable 52. Various instructions and the like for operating the endoscope 20 are input to the input device 50. The input device 50 may be composed of an operation panel provided on the insertion control apparatus 30. Alternatively, the input device 50 may be composed of a touch panel constituting a display screen of the display 40.

The insertion control apparatus 30 has a function of controlling the endoscope 20; a function of acquiring various kinds of information through the input device 50; and a function of outputting various kinds of information to the display 40. The insertion control apparatus 30 includes, for example, a computer. Specifically, the insertion control apparatus 30 includes a processor configured to operate according to pre-programmed software, and a storage device configured to store software and necessary information. Various circuits to be described later (e.g. an image processing circuit 76, a stiffness control circuit 86, and a shape calculation circuit 96) in the insertion control apparatus 30 are constituted by combinations of processors and storage devices. Alternatively, various circuits in the insertion control apparatus 30 may be constituted by combining dedicated circuits and/or general-purpose circuits.

FIG. 2 shows functional blocks of the flexible tube insertion apparatus 10 shown in FIG. 1. As shown in FIG. 2, the flexible tube insertion apparatus 10 includes an illumination system 60 for illuminating an observation target, and an imaging system 70 for imaging the observation target.

The illumination system 60 includes a light source device 62 configured to emit light for illuminating the observation target; a light guide member 64 configured to guide light emitted from the light source device 62; and a light emission unit 66 configured to emit light guided by the light guide member 64 to the outside of the endoscope 20.

The light source device 62 is disposed inside the insertion control apparatus 30. The light guide member 64 extends in the inside of the endoscope 20. To be more specific, the light guide member 64 extends from the connection portion 28 that is detachably attached to the insertion control apparatus 30, passes through the inside of the universal cord 26, control section 22, and insertion section 24, and extends up to the hard distal section 24a. The light guide member 64 may be composed of, for example, a single optical fiber, or a bundle fiber in which optical fibers are bundled. The light emission unit 66 is disposed in the hard distal section 24a and is optically connected to the light guide member 64.

In other words, the light source device 62 cooperates with the endoscope 20, to be more specific, the light guide member 64 and light emission unit 66 in the endoscope 20, to constitute the illumination system 60.

Light emitted from the light source device 62 enters the light guide member 64. The light entering the light guide member 64 is guided by the light guide member 64, and enters the light emission unit 66. The light entering the light emission unit 66 is emitted to the outside of the endoscope 20 by the light emission unit 66. The light emitted to the outside of the endoscope 20 is, for example, applied to an observation target. The light applied to the observation target is, for example, reflected or scattered by the observation target.

The imaging system 70 includes an imaging element 72 configured to acquire an optical image of the observation target illuminated by the illumination system 60; and an image processing circuit 76 configured to process an image signal of the optical image of the observation target acquired by the imaging element 72. The imaging element 72 is disposed in the hard distal section 24a. The image processing circuit 76 is disposed inside the insertion control apparatus 30. The imaging element 72 is electrically connected to the image processing circuit 76, for example, by an imaging cable 74.

The image signal of the optical image of the observation target acquired by the imaging element 72 is supplied to the image processing circuit 76. The image processing circuit 76 executes a necessary image process on the supplied image signal, and supplies the image-processed image signal to the display 40. The display 40 displays an image in accordance with the supplied image signal.

For the purpose of convenience, the insertion control apparatus 30 is described here as including the light source device 62 and the image processing circuit 76, but the insertion control apparatus 30 does not necessarily need to include the light source device 62 and the image processing circuit 76. The light source device 62 and the image processing circuit 76 may be constituted separately from the insertion control apparatus 30.

The flexible tube insertion apparatus 10 further includes a stiffness control system 80 configured to control the stiffness of various portions of the soft tube 24c of the insertion section 24; and a shape calculation system 90 configured to calculate the shape of the insertion section 24.

The stiffness control system 80 includes stiffness changing devices 82, and a stiffness control circuit 86 configured to independently control the stiffness changing devices 82. The stiffness changing devices 82 are arranged on the soft tube 24c along the longitudinal axis of the insertion section 24. Each stiffness changing device 82 is configured to be able to change the stiffness of that portion of the soft tube 24c on which the stiffness changing device 82 is provided. The details of the stiffness control system 80 will be described later.

The shape calculation system 90 includes a shape sensor 92 configured to acquire shape information of various portions of the insertion section 24; and a shape calculation circuit 96 configured to calculate the shape of the entirety of the insertion section 24, based on the shape information of the various portions of the insertion section 24 acquired by the shape sensor 92. The details of the shape calculation system 90 will be described later.

The insertion control apparatus 30 includes a bend detection circuit 110 configured to detect formation of two bend portions in the soft tube 24c; and a positional relationship calculation circuit 140 configured to calculate a three-dimensional positional relationship between the two bend portions. The details of the bend detection circuit 110 and the positional relationship calculation circuit 140 will be described later.

Configuration Example 1 of Stiffness Control System

Figure 3:
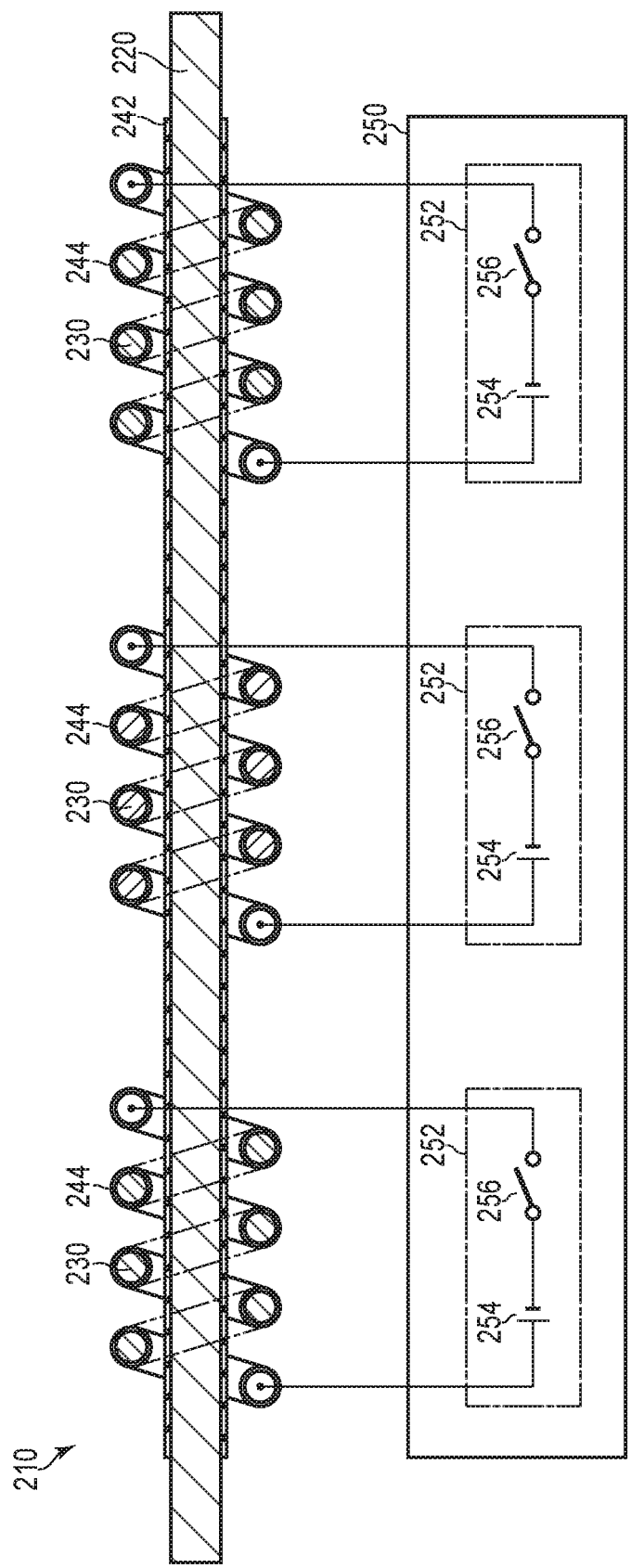
FIG. 3 shows a stiffness changing device and a stiffness control circuit in a configuration example of a stiffness control system shown in FIG. 2.

FIG. 3 shows a stiffness changing device 210 and a stiffness control circuit 250 in a configuration example of the stiffness control system 80. As illustrated in FIG. 3, the stiffness changing device 210 has a function of providing different stiffness to the soft tube 24c by taking different stiffness states. The stiffness changing device 210 includes a shape memory member 220 capable of transitioning in phase between a first phase and a second phase, and inducing members 230 that are configured to induce the shape memory member 220 to transition in phase between the first phase and second phase.

When the shape memory member 220 is in the first phase, the shape memory member 220 takes a soft state in which the shape memory member 220 can easily deform in accordance with external force, i.e. the shape memory member 220 exhibits a low elastic coefficient, so as to provide a relatively low stiffness to the soft tube 24c. When the shape memory member 220 is in the second phase, the shape memory member 220 takes a hard state in which the shape memory member 220 tends to take a memorized shape that is memorized in advance against external force, i.e. the shape memory member 220 exhibits a high elastic coefficient, so as to provide a relatively high stiffness to the soft tube 24c.

Each inducing member 230 has a capability of generating heat. The shape memory member 220 has a characteristic of transitioning in phase from the first phase to the second phase on heating the inducing member 230.

The shape memory member 220 is elongated, and the inducing members 230 are arranged at intervals along the longitudinal axis of the shape memory member 220.

The shape memory member 220 may be composed of, for example, a shape memory alloy. The shape memory member 220 may be, for example, an alloy including NiTi, although the shape memory member 220 is not limited to this. Besides, the shape memory member 220 may be composed of some other material, such as a shape memory polymer, a shape memory gel, or a shape memory ceramic.

The inducing member 230 may be composed of, for example, a heater. Specifically, the inducing member 230 may have a characteristic of generating heat by the supply of current flowing in the inducing member 230. The inducing member 230 may be, for example, a heating wire, i.e. an electrically conductive member with a high electrical resistance. The inducing member 230 only needs to have a capability of generating heat, and may be composed of, aside from a heater, an imaging element, a light guide, or some other element or member. Furthermore, the inducing member 230 may be composed of a structure configured to generate heat by a chemical reaction.

The shape memory member 220 may be composed of an electrically conductive material. For example, an insulating film 242 is provided around the shape memory member 220. The insulating film 242 functions to prevent short-circuit between the shape memory member 220 and the inducing member 230.

The inducing member 230 may be composed of an electrically conductive material. For example, an insulating film 244 is provided around the inducing member 230. The insulating film 244 functions to prevent short-circuit between the shape memory member 220 and the inducing member 230 and short-circuit between neighboring portions of the inducing member 230.

The stiffness control circuit 250 includes driving circuits 252 that are configured to respectively drive the inducing members 230. Each driving circuit 252 includes a power source 254 and a switch 256. Each driving circuit 252 is electrically connected across the corresponding inducing member 230. Each driving circuit 252 supplies current to the corresponding inducing member 230 in accordance with ON of the switch 256, i.e. a closing operation of the switch 256, and stops the supply of current to the corresponding inducing member 230 in accordance with OFF of the switch 256, i.e. an opening operation of the switch 256. The inducing member 230 generates heat in accordance with the supply of current.

The shape memory member 220 may have a wire shape. The inducing member 230 is disposed near the shape memory member 220. The inducing member 230 may have a coil shape, and the shape memory member 220 may extend through the inside of the coil-shaped inducing member 230.

When the switch 256 of the driving circuit 252 is in the OFF state, the shape memory member 220 is in the first phase, which corresponds to the soft state in which the elastic coefficient is low. In the first phase, the shape memory member 220 is in the state in which the shape memory member 220 easily deforms in accordance with external force.

If the switch 256 of the driving circuit 252 is changed over into the ON state, current flows in the inducing member 230, and the inducing member 230 generates heat. As a result, the shape memory member 220 transitions in phase into the second phase, which corresponds to the hard state in which the elastic coefficient is high. In the second phase, the shape memory member 220 exhibits a tendency to take a memorized shape.

When the shape memory member 220 is in the first phase, the stiffness changing device 210 provides a relatively low stiffness to the soft tube 24c, and the shape memory member 220 easily deforms in accordance with external force acting on the soft tube 24c, i.e. the force that can deform the shape memory member 220.

When the shape memory member 220 is in the second phase, the stiffness changing device 210 provides a relatively high stiffness to the soft tube 24c, and the shape memory member 220 exhibits a tendency to return to the memorized shape against the external force acting on the soft tube 24c, i.e. the force that can deform the shape memory member 220.

For example, the phase of a part of the shape memory member 220, which is located near each inducing member 230, is switched between the first phase and the second phase by the stiffness control circuit 250, so that the stiffness of the soft tube 24c is switched. The supply of current to the inducing members 230 is independently switched by the stiffness control circuit 250, so shat the phases of parts of the shape memory member 220 are independently switched. Accordingly, the stiffness of parts of the soft tube 24c is independently switched. Thereby, the stiffness changing device 210 can provide a desired complex stiffness distribution to the soft tube 24c.

Configuration Example 2 of Stiffness Control System

Figure 4:
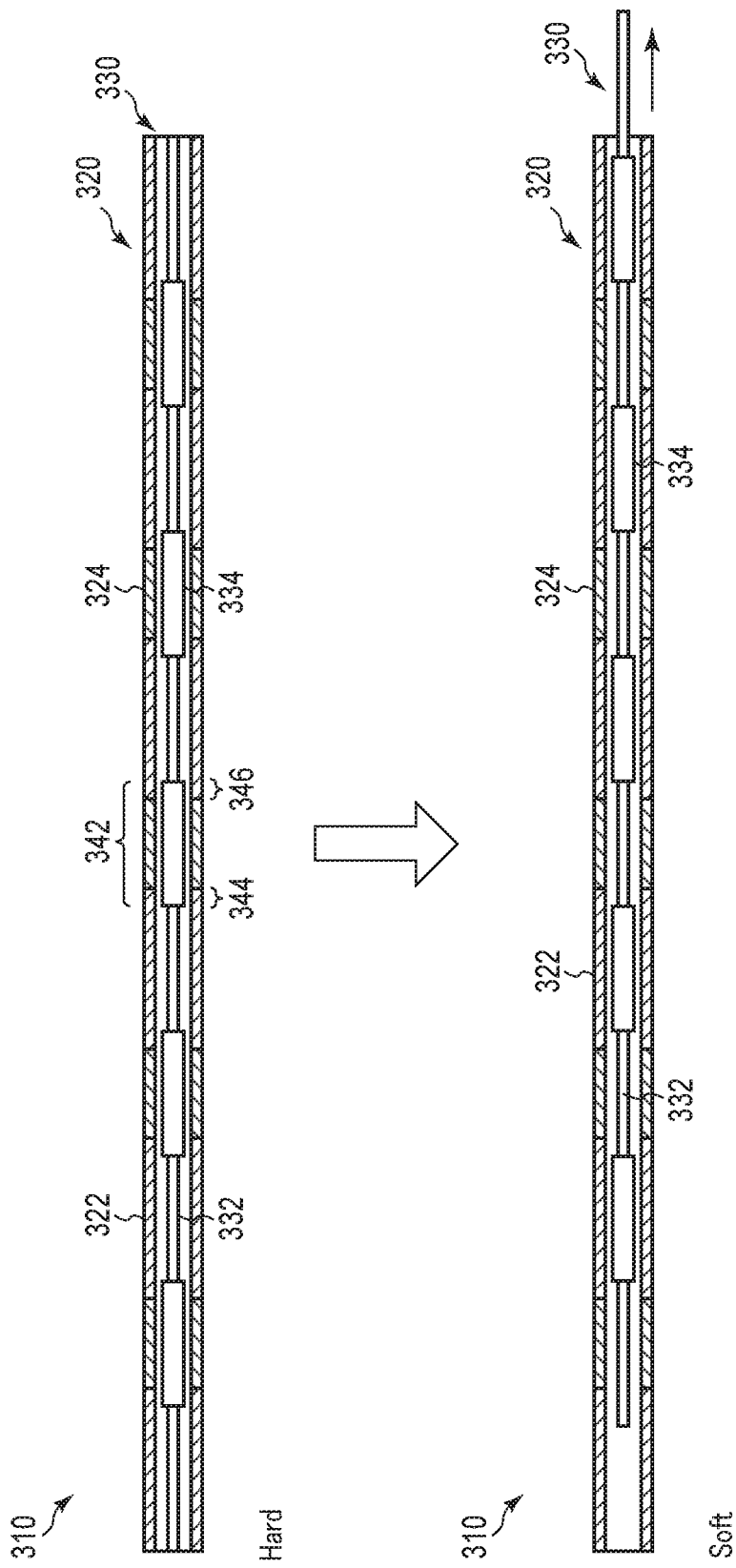
FIG. 4 shows a stiffness changing device in another configuration example of the stiffness control system shown in FIG. 2.

FIG. 4 shows a stiffness changing device 310 in another configuration example of the stiffness control system 80.

FIG. 4 shows the state of switching of stiffness of the stiffness changing device 310 from a high stiffness state to a low stiffness state. In FIG. 4, the stiffness changing device 310 in the high stiffness state is depicted in an upper part of FIG. 4, and the stiffness changing device 310 in the low stiffness state is depicted in a lower part of FIG. 4.

The stiffness changing device 310 is a device for providing different stiffness to the soft tube 24c, which is the object of attachment. The stiffness changing device 310 includes a first longitudinal member 320 and a second longitudinal member 330. The second longitudinal member 330 is disposed adjacently along the first longitudinal member 320. For example, the first longitudinal member 320 is composed of an outer tube, and the second longitudinal member 330 is composed of a core member disposed inside the outer tube. For example, the outer tube has an annular cross-sectional shape perpendicular to the axis, and the core member has a circular outer peripheral shape in cross section perpendicular to the axis. In this case, stable flexural stiffness is provided with respect to bending in all directions.

The first longitudinal member 320 includes high flexural stiffness portions 322 and low flexural stiffness portions 324. For example, the first longitudinal member 320 includes six high flexural stiffness portions 322 and five low flexural stiffness portions 324. The high flexural stiffness portions 322 and low flexural stiffness portions 324 are successively and alternately arranged along the axis of the first longitudinal member 320. The high flexural stiffness portion 322 has a flexural stiffness higher than a flexural stiffness of the low flexural stiffness portion 324. Thus, the first longitudinal member 320 is relatively easily bendable at the low flexural stiffness portion 324, and is relatively less easily bendable at the high flexural stiffness portion 322.

The second longitudinal member 330 includes non-bend-restriction portions 332 and bend-restriction portions 334. For example, the second longitudinal member 330 includes six non-bend-restriction portions 332 and five bend-restriction portions 334. The non-bend-restriction portions 332 and bend-restriction portions 334 are successively and alternately arranged along the axis of the second longitudinal member 330. The bend-restriction portion 334 has a flexural stiffness higher than a flexural stiffness of the non-bend-restriction portion 332. Thus, the second longitudinal member 330 is relatively easily bendable at the non-bend-restriction portion 332, and is relatively less easily bendable at the bend-restriction portion 334. For example, the non-bend-restriction portion 332 is composed of a small-diameter portion having a relatively small diameter, and the bend-restriction portion 334 is composed of a large-diameter portion having a relatively large diameter. The bend-restriction portion 334 has, for example, a uniform thickness from an end portion to the other end portion thereof.

In the stiffness changing device 310, the relative position of the second longitudinal member 330 to the first longitudinal member 320 is changed, which allows the flexural stiffness of the stiffness changing device in the low flexural stiffness portion 324 to be switched between a high stiffness state in which the flexural stiffness is relatively high and a low stiffness state in which the flexural stiffness is relatively low.

The switching from the high stiffness state to the low stiffness state is effected by relative movement of the second longitudinal member 330 to the first longitudinal member 320 along the axis of the first longitudinal member 320.

In the high stiffness state, the bend-restriction portion 334 of the second longitudinal member 330 is disposed in a range including the low flexural stiffness portion 324 of the first longitudinal member 320. The bend-restriction portion 334 restricts the bend of the low flexural stiffness portion 324 of the first longitudinal member 320. In this manner, as a result of that the second longitudinal member 330 restricts the bend of the first longitudinal member 320, the stiffness changing device 310 is in the high stiffness state, i.e. the hard state.

In the low stiffness state, the non-bend-restriction portion 332 of the second longitudinal member 330 is disposed in the range including the low flexural stiffness portion 324 of the first longitudinal member 320. Compared to the bend-restriction portion 334, the non-bend-restriction portion 332 has a lower degree by which the non-bend-restriction portion 332 restricts the bend of the low flexural stiffness portion 324 of the first longitudinal member 320. Thus, the stiffness changing device 310 is in the low stiffness state, i.e. the soft state, in which the stiffness changing device 310 is easily bendable at the low flexural stiffness portion 324.

According to another point of view, the first longitudinal member 320 includes a restricted portion 342 in which bending is restricted by the bend-restriction portion 334 in the high stiffness state. The restricted portion 342 includes a portion 344 of a first high flexural stiffness portion 322 of the first longitudinal member 320, the low flexural stiffness portion 324 neighboring the first high flexural stiffness portion 322, and a portion 346 of a second high flexural stiffness portion 322 that, together with the first high flexural stiffness portion 322, sandwiches the low flexural stiffness portion 324. In other words, the restricted portion 342 includes a low flexural stiffness portion 324, a portion 344 of a high flexural stiffness portion 322 located on one side of the low flexural stiffness portion 324, e.g. on the left side in FIG. 4, and a portion 346 of a high flexural stiffness portion 322 located on the other side of the low flexural stiffness portion 324, e.g. on the right side in FIG. 4. The length of the restricted portion 342, i.e. the dimension of the restricted portion 342 along the axis of the first longitudinal member 320, is equal to the length of the bend-restriction portion 334, i.e. the dimension of the bend-restriction portion 334 along the axis of the second longitudinal member 330.

When the bend-restriction portion 334 is located at a position corresponding to the restricted portion 342, the bend-restriction portion 334 restricts the bend of the low flexural stiffness portion 324. On the other hand, when the non-bend-restriction portion 332 is located at a position corresponding to the restricted portion 342, the non-bend-restriction portion 332 less restricts the bend of the low flexural stiffness portion 324 than when the bend-restriction portion 334 is located at the position corresponding to the restricted portion 342. Accordingly, when the bend-restriction portion 334 is located at the position corresponding to the restricted portion 342, the flexural stiffness of the stiffness changing device 310 in the region of the restricted portion 342 is higher than when the non-bend-restriction portion 332 is located at the position corresponding to the restricted portion 342.

A gap is provided between the first longitudinal member 320 and the bend-restriction portion 334 of the second longitudinal member 330. In this case, in the high stiffness state, when the magnitude of bend of the restricted portion 342 becomes equal to or higher than a restriction occurrence point that is a specific magnitude of bend, the bend-restriction portion 334 restricts an increase of bend of the restricted portion 342, and enhances the flexural stiffness of the stiffness changing device 310 at the restricted portion 342. As a result, although the flexural stiffness of the stiffness changing device 310 remains low at the beginning of bending, the flexural stiffness sharply increases when the bend increases by a predetermined magnitude or more and thereby the gap no longer exists.

In this manner, the relative movement between the first longitudinal member 320 and second longitudinal member 330 allows the stiffness of the stiffness changing device 310 to be switched between the high stiffness state, i.e. the hard state, and the low stiffness state, i.e. the soft state.

In the low stiffness state, the first longitudinal member 320 is easily bendable in the low flexural stiffness portion 324. By contrast, in the high stiffness state, the first longitudinal member 320 is less easily bendable even in the low flexural stiffness portion 324. Accordingly, it can be said that the switching between the low stiffness state and the high stiffness state in the stiffness changing device 310 is a movement of locking or unlocking a joint.

Configuration Example 3 of Stiffness Control System

Figure 5:
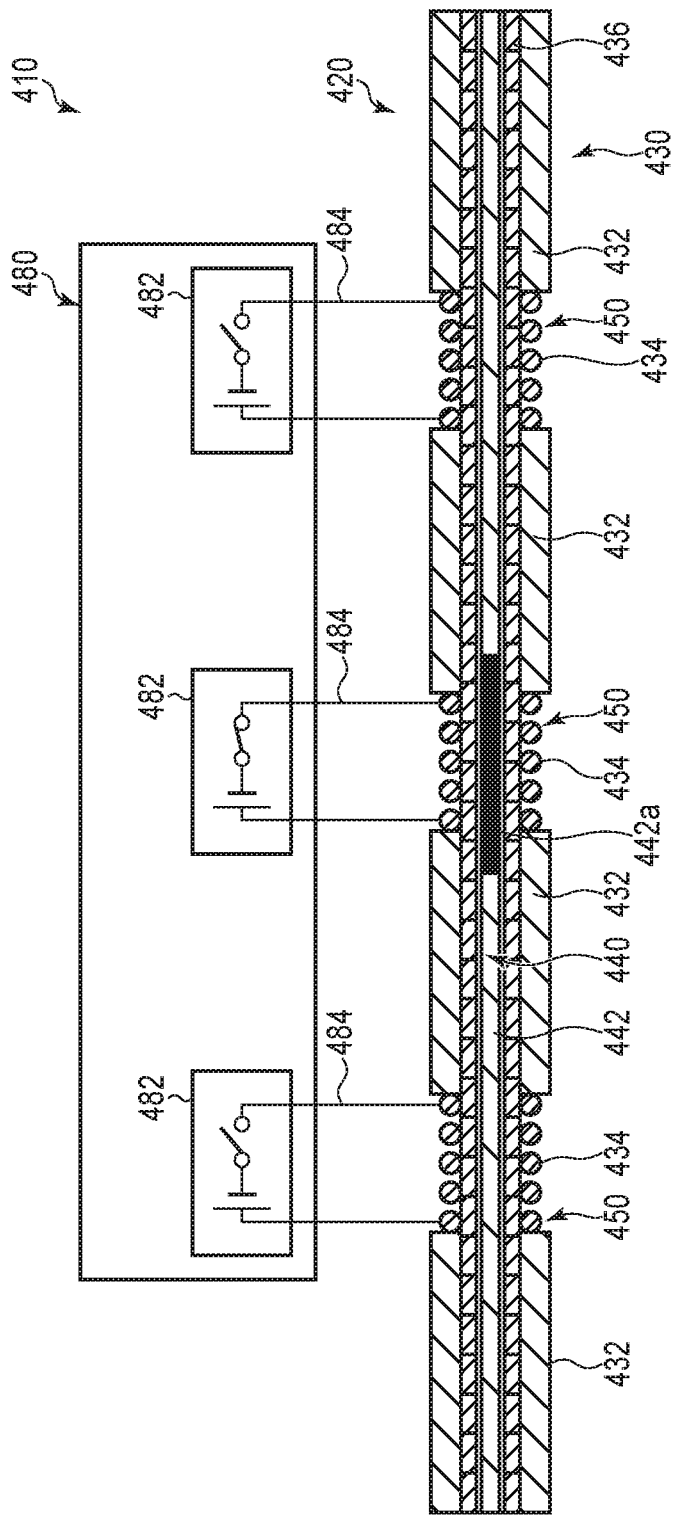
FIG. 5 shows a stiffness control system according to another configuration example of the stiffness control system shown in FIG. 2.

FIG. 5 shows a stiffness control system 410 according to another configuration example of the stiffness control system 80. As illustrated in FIG. 5, the stiffness control system 410 includes a stiffness changing device 420 that is to be attached to the soft tube 24c, and a control device 480 configured to control the stiffness changing device 420. In a shape memory member 442, a part (to-be-heated portion 442a) that is in the high stiffness state (hard state) is indicated by solid paint in black.

The stiffness changing device 420 provides different stiffness to the soft tube 24c to change the stiffness of the soft tube 24c. The stiffness changing device 420 includes a first longitudinal member 430, a second longitudinal member 440 disposed along the first longitudinal member 430, and inducers 450. For example, the first longitudinal member 430 is an outer cylinder, and the second longitudinal member 440 is a core member disposed inside the first longitudinal member 430. For example, the cross-sectional shape of the outer cylinder perpendicular to the longitudinal axis of outer cylinder is an annular shape, and the outer periphery in cross section of the core member perpendicular to the longitudinal axis of the core member is a circular shape. In this case, the stiffness changing device 420 provides a stable flexural stiffness with respect to bending in all directions.

The first longitudinal member 430 includes at least one high flexural stiffness portion 432 with a relatively high flexural stiffness, and at least one low flexural stiffness portion 434 with a relatively low flexural stiffness. Specifically, the flexural stiffness of the high flexural stiffness portion 432 is high, and the flexural stiffness of the low flexural stiffness portion 434 is lower than the flexural stiffness of the high flexural stiffness portion 432. The first longitudinal member 430 further includes a cylindrical outer support member 436 supporting the high flexural stiffness portion 432 and low flexural stiffness portion 434. The flexural stiffness of the outer support member 436 is lower than the flexural stiffness of the high flexural stiffness portion 432. Thus, the first longitudinal member 430 is relatively easily bendable at the low flexural stiffness portion 434, and is relatively less easily bendable at the high flexural stiffness portion 432.

The high flexural stiffness portion 432, low flexural stiffness portion 434, and outer support member 436 are separate from each other. The high flexural stiffness portion 432 is composed of, for example, a cylindrical member such as a metallic pipe. The low flexural stiffness portion 434 is composed of, for example, a coil member such as a non-densely wound coil. The outer support member 436 is composed of, for example, a coil member such as a densely wound coil. The high flexural stiffness portion 432 is a cylindrical hard portion having a high flexural stiffness, and the low flexural stiffness portion 434 and outer support member 436 are cylindrical soft portions with low flexural stiffness.

The outer support member 436 is disposed inside the high flexural stiffness portion 432 and low flexural stiffness portion 434. An outer peripheral surface of the outer support member 436 is fixed by adhesion to an inner peripheral surface of the high flexural stiffness portion 432. The high flexural stiffness portions 432 are arranged at intervals in the longitudinal axis direction of the first longitudinal member 430. The low flexural stiffness portions 434 are arranged in spaces between the high flexural stiffness portions 432 in the longitudinal axis direction of the first longitudinal member 430. Accordingly, the high flexural stiffness portions 432 and the low flexural stiffness portion 434 are alternately arranged in the longitudinal axis direction of the first longitudinal member 430. An end portion of the low flexural stiffness portion 434 is fixed to an end portion of the high flexural stiffness portions 432 that neighbors the end portion of the low flexural stiffness portion 434. The low flexural stiffness portion 434 is wound around the outer support member 436 in the space between the high flexural stiffness portions 432.

The outer support member 436 extends over the entire length of the stiffness changing device 420. The outer support member 436 is helically disposed. For example, the outer support member 436 functions as a core member for the high flexural stiffness portions 432 and low flexural stiffness portion 434.

The second longitudinal member 440 extends over the entire length of the stiffness changing device 420. The second longitudinal member 440 is disposed inside the outer support member 436. An outer peripheral surface of the second longitudinal member 440 is not in contact with an inner peripheral surface of the outer support member 436, and a space is formed between the outer support member 436 and the second longitudinal member 440.

The second longitudinal member 440 includes at least a shape memory member 442 capable of transitioning in phase by heat between a first phase and a second phase. When the phase of the shape memory member 442 is the first phase, the shape memory member 442 takes a low stiffness state in which the shape memory member 442 can easily deform in accordance with external force, and exhibits a low elastic coefficient. Accordingly, when the phase of the shape memory member 442 is the first phase, the shape memory member 442 provides a relatively low stiffness to the soft tube 24c. In the first phase, the stiffness changing device 420 and the soft tube 24c can easily bend, for example, by external force.

When the phase of the shape memory member 442 is the second phase, the shape memory member 442 takes a high stiffness state having a higher stiffness than the low stiffness state, and exhibits a high elastic coefficient. Accordingly, when the phase of the shape memory member 442 is the second phase, the shape memory member 442 takes a high stiffness state indicative of a tendency that the shape memory member 442 takes a memorized shape that is memorized in advance against external force, and provides a relatively high stiffness to the soft tube 24c. The memorized shape may be, for example, a linear shape. In the second phase, the stiffness changing device 420 and the soft tube 24c can maintain, for example, a substantially linear state, or can be bent more gently by external force than in the first phase.

When the phase of the shape memory member 442 is the first phase, the flexural stiffness of the shape memory member 442 is lower than the flexural stiffness of the high flexural stiffness portion 432 and is equal to or lower than the flexural stiffness of the low flexural stiffness portion 434. When the phase of the shape memory member 442 is the second phase, the flexural stiffness of the shape memory member 442 is equal to or lower than the flexural stiffness of the high flexural stiffness portion 432 and is higher than the flexural stiffness of the low flexural stiffness portion 434.

The low flexural stiffness portion 434 is composed of an electrically conductive material. The low flexural stiffness portion 434 may be, for example, a heating wire, i.e. an electrically conductive member with a high electrical resistance. For example, an insulating film (not shown) is provided around the low flexural stiffness portion 434. The insulating film prevents short-circuit between the low flexural stiffness portion 434 and the outer support member 436, and short-circuit between the high flexural stiffness portion 432 and the low flexural stiffness portion 434.

For example, an insulating film (not shown) is provided around the outer support member 436. The insulating film prevents short-circuit between the low flexural stiffness portion 434 and the outer support member 436, short-circuit between the high flexural stiffness portion 432 and the outer support member 436, and short-circuit between the outer support member 436 and the shape memory member 442.

The inducer 450 has a capability of generating heat by receiving the supply of current from the control device 480. The inducer 450 transmits the heat to a part of the shape memory member 442, the part being located near the inducer 450. In addition, in this part, the inducer 450 induces the shape memory member 442 to transition in phase between the first phase and the second phase. The inducer 450 changes the stiffness of a part of the second longitudinal member 440 in the longitudinal axis direction of the second longitudinal member 440.

The control device 480 includes driving units 482 configured to independently drive the low flexural stiffness portions 434. The driving unit 482 includes a power source and a switch. The driving unit 482 is electrically connected across the low flexural stiffness portion 434 through wirings 484. The driving unit 482 supplies current to the low flexural stiffness portion 434 through the wirings 484 in accordance with an ON operation of the switch, and stops the supply of current to the low flexural stiffness portion 434 in accordance with an OFF operation of the switch.

The low flexural stiffness portion 434 has a capability of generating heat in accordance with the supply of current from the control device 480. The heat generation quantity of the low flexural stiffness portion 434 depends on the supply quantity of current. The low flexural stiffness portion 434 functions as the inducer 450 configured to induce the shape memory member 442 by heat to transition in phase between the first phase and the second phase. To be more specific, the low flexural stiffness portion 434 functions as a coil heater that is a heating unit that is configured to heat the shape memory member 442 through the outer support member 436. The shape memory member 442 has a characteristic of transitioning in phase from the first phase to the second phase by the heat generated from the low flexural stiffness portion 434 functioning as the inducer 450.

In the stiffness control system 410, in the initial state, the driving unit 482 does not supply current to the low flexural stiffness portion 434, so that the low flexural stiffness portion 434 generates no heat, and the shape memory member 442 and the soft tube 24c are in the low stiffness state over the entire length.

The driving unit 482 supplies current to the low flexural stiffness portion 434 through the wirings 484 in accordance with the ON operation of the switch. The low flexural stiffness portion 434 generates heat in accordance with the supply of current. The heat is indirectly transmitted from the low flexural stiffness portion 434 to the shape memory member 442. The transmission of heat raises the temperature of the to-be-heated portion 442a of the shape memory member 442. The phase of the to-be-heated portion 442a changes from the first phase to second phase by the heating, and the to-be-heated portion 442a is switched from the low stiffness state to the high stiffness state. Thereby, the soft tube 24c is partly switched from the low stiffness state to the high stiffness state. The part of the soft tube 24c that is in the high stiffness state maintains a substantially linear state against the external force acting on the soft tube 24c, i.e. the force that can deform the shape memory member 442.

The driving unit 482 stops the supply of current to the low flexural stiffness portion 434 in accordance with the OFF operation of the switch. Then, the temperature of the to-be-heated portion 442a lowers by natural cooling, the phase of the to-be-heated portion 442a changes from the second phase to the first phase, and the stiffness of the to-be-heated portion 442a lowers. Further, the stiffness of the part of the soft tube 24c at which the to-be-heated portion 442a is located also lowers. Accordingly, the soft tube 24c can easily be bent by external force.

In this manner, the phase of a part of the shape memory member 442 is switched between the first phase and the second phase by, for example, the low flexural stiffness portion 434, so that the stiffness of a part of the soft tube 24c is switched.

Configuration Example 4 of Stiffness Control System

Figure 6:
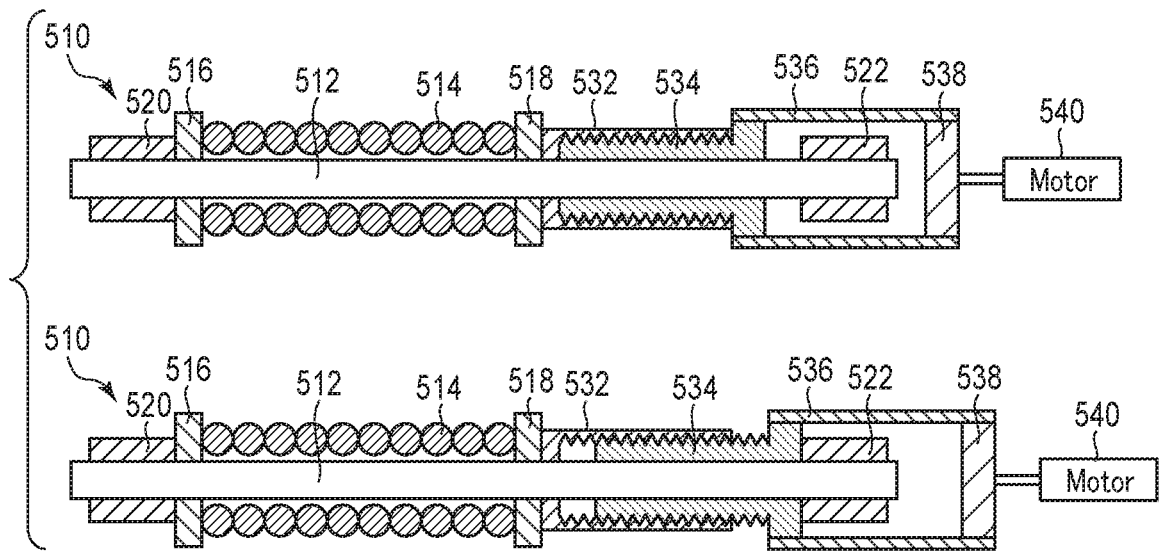
FIG. 6 shows a basic configuration of a stiffness changing device in another configuration example of the stiffness control system shown in FIG. 2.

FIG. 6 shows a basic configuration of a stiffness changing device 510 according to another configuration example of the stiffness control system 80. An upper part of FIG. 6 shows the stiffness changing device 510 in a low flexural stiffness state, and a lower part of FIG. 6 shows the stiffness changing device 510 in a high flexural stiffness state.

The stiffness changing device 510 includes a coil pipe 514 with flexibility, for example, a densely wound coil; a core 512 extending in the inside of the coil pipe 514; and a pair of stationary members 520 and 522 that are disposed on both sides of the coil pipe 514 and are fixed to the core 512.

A washer 516 is disposed between the coil pipe 514 and the stationary member 520. A washer 518 is disposed between the coil pipe 514 and the stationary member 522. The washers 516 and 518 function to restrict the movement of the coil pipe 514 along the core 512. The washers 516 and 518 prevent the coil pipe 514 from dropping off the core 512, and prevent the stationary members 520 and 522 from biting into the coil pipe 514.

The stiffness changing device 510 also includes an adjusting mechanism configured to adjust gaps between the coil pipe 514 and the stationary members 520 and 522. The adjusting mechanism is composed of a pulling mechanism configured to pull at least one of the paired stationary members 520 and 522 in a direction in which the paired stationary members 520 and 522 move away from each other. The pulling mechanism includes a nut 532, a lead screw 534 that is screwed with the nut 532, a cylindrical body 536 fixed to the lead screw 534, a cover 538 fixed to the cylindrical body 536, and a motor 540 configured to rotate the lead screw 534.

The core 512 extends through the nut 532 and lead screw 534. The stationary member 522 is contained in the cylindrical body 536. The motor 540 is supported so that the motor 540 itself does not rotate and is movable in the axial direction. Rotating the lead screw 534 relative to the nut 532 by the motor 540 causes the lead screw 534 to move along the axis of the core 512.

In the state shown in the upper part of FIG. 6, there is a gap between the lead screw 534 and the stationary member 522. In this state, the core 512 is movable along the coil pipe 514. This state is a state with low flexural stiffness because no tensile stress acts on the core 512 when the coil pipe 514 is bent. The stiffness changing device 510 that is in the low flexural stiffness provides a low stiffness to the soft tube 24c on which the stiffness changing device 510 is attached.

On the other hand, in the state shown in the lower part of FIG. 6, there is no gap between the lead screw 534 and the stationary member 522. In this state, the core 512 is immovable relative to the coil pipe 514. In addition, the lead screw 534 pushes the stationary member 522, so that tensile stress acts on the core 512. This state is a state with high flexural stiffness because tensile stress acts on the core 512 when the coil pipe 514 is bent. The stiffness changing device 510 that is in the high flexural stiffness provides a high stiffness to the soft tube 24c on which the stiffness changing device 510 is attached.

Configuration Example 5 of Stiffness Control System

Figure 7:
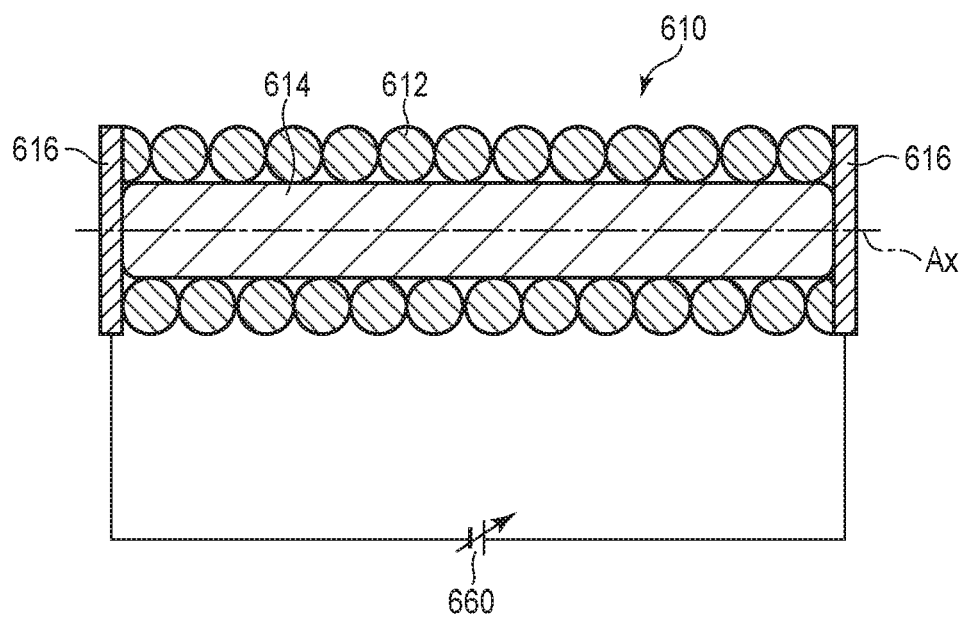
FIG. 7 schematically shows a stiffness changing device and a stiffness control circuit in another configuration example of the stiffness control system shown in FIG. 2.

FIG. 7 schematically shows a stiffness changing device 610 and a stiffness control circuit 660 according to another configuration example of the stiffness control system 80. As shown in FIG. 7, the stiffness changing device 610 includes a coil pipe 612, a conducting-polymer artificial muscle 614 located in the coil pipe 612, and a pair of electrodes 616 provided on both ends of the coil pipe 612. The stiffness changing device 610 is built in the soft tube 24c so that a center axis Ax of the coil pipe 612 coincides with, or is parallel to, a center axis of the soft tube 24c.

The electrodes 616 of the stiffness changing device 610 are electrically connected across the stiffness control circuit 660. The stiffness control circuit 660 applies voltage to the conducting-polymer artificial muscle 614 through the electrodes 616. The application of voltage causes the conducting-polymer artificial muscle 614 to try to expand its diameter about the center axis Ax of the coil pipe 612, but the expansion of the diameter of the conducting-polymer artificial muscle 614 is restricted by the coil pipe 612. Thus, as the value of applied voltage becomes higher, the flexural stiffness of the stiffness changing device 610 increases. Specifically, changing the stiffness of the stiffness changing device 610 also changes the flexural stiffness of the soft tube 24c, in which the stiffness changing device 610 is built.

Configuration Example 1 of Shape Calculation System

Figure 8:
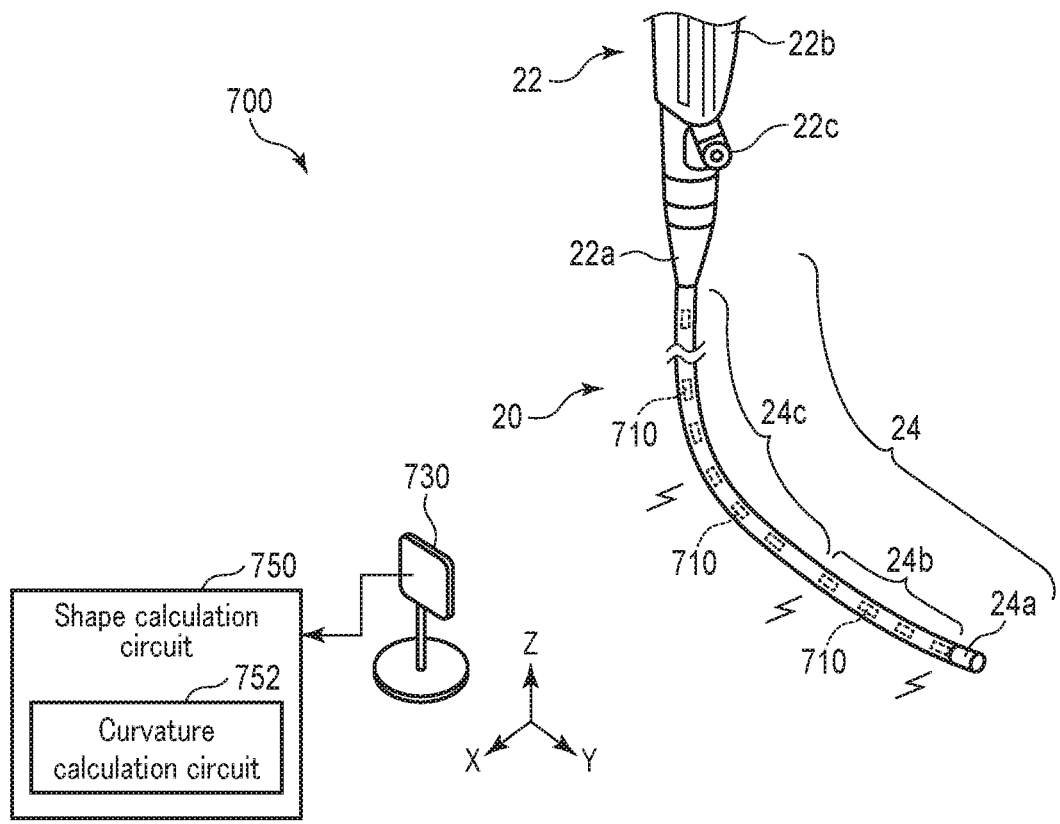
FIG. 8 schematically shows a shape calculation system according to a configuration example of a shape calculation system shown in FIG. 2.

A configuration example of the shape calculation system 90 will be described. FIG. 8 schematically shows a shape calculation system 700 according to the present configuration example. The shape calculation system 700 includes a large number of position sensors 710 that are built in at intervals along the longitudinal axis of the insertion section 24. As the position sensors 710, there are known magnetic-type, ultrasonic-type, and optical-type position sensors. For example, the position sensor 710 is composed of a magnetic coil. The magnetic coil is a magnetic field generating element configured to generate a magnetic field.

FIG. 8 schematically shows an example in which the position sensors 710 are composed of magnetic coils. The shape calculation system 90 includes an antenna 730 configured to receive signals from the position sensors 710, i.e. magnetic fields generated by the magnetic field generating elements. The antenna 730 is separate from the endoscope 20, and is fixed to a vicinity of an observation target into which the insertion section 24 of the endoscope 20 is inserted. The antenna 730 is connected to a shape calculation circuit 750.

The position sensors 710 and antenna 730 correspond to the shape sensor 92 of the shape calculation system 90 shown in FIG. 2. The shape calculation circuit 750 corresponds to the shape calculation circuit 96 of the shape calculation system 90 shown in FIG. 2.

Based on signals, i.e. information of magnetic fields, received by the antenna 730, the shape calculation circuit 750 calculates positions of the position sensors 710 in a coordinate space determined based on the antenna 730. Further, based on the information of positions of the position sensors 710, the shape calculation circuit 750 calculates a bend shape of the insertion section 24, for example, by interpolating coordinates of the positions of the position sensors 710. The shape calculation circuit 750 includes, if necessary, a curvature calculation circuit 752 configured to calculate the curvature of various portions of the insertion section 24 at which many position sensors 710 are built.

Accordingly, the shape calculation system 700 can recognize a spatial position, i.e. a three-dimensional position, of various portions of the insertion section 24 relative to a predetermined reference point.

Configuration Example 2 of Shape Calculation System

Figure 9:
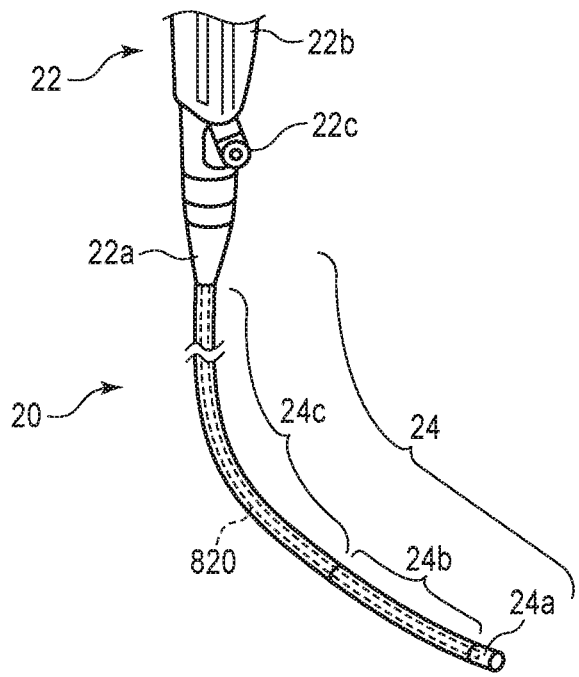
FIG. 9 shows another configuration example of a shape sensor of the shape calculation system shown in FIG. 2.

FIG. 9 shows another configuration example of the shape sensor 92 of the shape calculation system 90. In this configuration example, the shape sensor 92 includes a fiber sensor 820 provided along the longitudinal direction of the insertion section 24.

Figure 10:
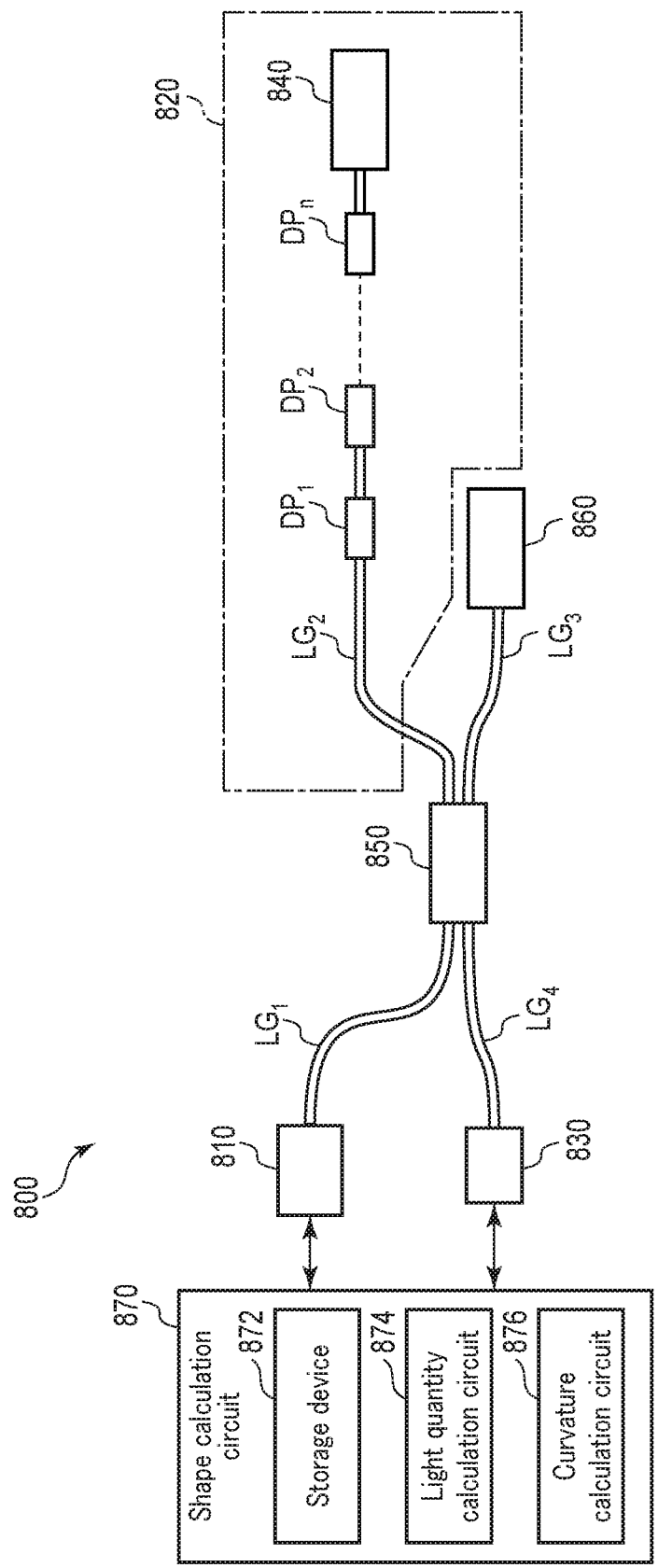
FIG. 10 shows a configuration of the shape calculation system including a fiber sensor shown in FIG. 9.

FIG. 10 shows a configuration of a shape calculation system 800 including the fiber sensor 820. The shape calculation system 800 includes the fiber sensor 820 assembled in the insertion section 24; a light source 810 configured to supply light to the fiber sensor 820; a light detector 830 configured to detect light that has passed through the fiber sensor 820; a light branching element 850 configured to guide light from the light source 810 to the fiber sensor 820 and to guide light from the fiber sensor 820 to the light detector 830; an antireflection member 860 connected to the light branching element 850; and a shape calculation circuit 870 configured to calculate the shape of the fiber sensor 820.

The fiber sensor 820 includes a light guide member $GL_2$ connected to the light branching element 850; bend sensors $DP_i$ (i=1, 2, . . . , n) provided on the light guide member $GL_2$; and a reflection member 840 provided on an end portion of the light guide member $GL_2$.

Each bend sensor $DP_i$ is composed of a material configured to reduce the quantity of light guided by the light guide member $GL_2$. The bend sensors $DP_i$ have functions of reducing the quantity of light of different wavelengths. Specifically, different bend sensors $DP_i$ have mutually different light absorption characteristics. Each bend sensor $DP_i$ is composed of, for example, a light absorber whose light absorptivity for light passing through each bend sensor $DP_i$ varies in accordance with a direction of bend and a curvature of bend. The light guide member $GL_2$ is composed of an optical fiber and has flexibility. The fiber sensor 820 is composed of a fiber sensor including an optical fiber on which the bend sensors $DP_i$ are provided.

The reflection member 840 has a function of reflecting light guided by the light guide member $GL_2$ from the light branching element 850 so as to return the light toward the light branching element 850.

The light source 810 is optically connected to the light branching element 850 through a light guide member $GL_1$. The light detector 830 is optically connected to the light branching element 850 through a light guide member $GL_4$. The antireflection member 860 is optically connected to the light branching element 850 through a light guide member $GL_3$. The light guide members $GL_1$, $GL_3$, and $GL_4$ are composed of, for example, optical fibers, and have flexibility.

The light source 810 has a function of supplying light to the fiber sensor 820. The light source 810 includes, for example, a generally known light emitting element such as a lamp, an LED, a laser diode, or the like.

The light branching element 850 guides light from the light source 810 to the fiber sensor 820 and guides light from the fiber sensor 820 to the light detector 830. The light branching element 850 includes an optical coupler, a half-mirror, etc. For example, the light branching element 850 divides the light emitted from the light source 810 and input through the light guide member $LG_1$, and guides the divided light to two light guide members $LG_2$ and $LG_3$. In addition, the light branching element 850 guides reflected light from the reflection member 840, which is input through the light guide member $LG_2$, to the light detector 830 through the light guide member $LG_4$.

The light detector 830 has a function of detecting light that has passed through the fiber sensor 820. The light detector 830 has a function of detecting the quantity of received light for each wavelength, i.e. a function of spectrally separating and detecting light. The light detector 830 detects the quantity of light in a predetermined wavelength range to output detection information. Here, the detection information is information representative of a relationship between a specific wavelength in the predetermined wavelength range and the quantity of light of the specific wavelength.

The fiber sensor 820, light source 810, light detector 830, light branching element 850, antireflection member 860, and light guide members $LG_1$, $LG_2$, $LG_3$ and $LG_4$ correspond to the shape sensor 92 of the shape calculation system 90 shown in FIG. 2. In addition, the shape calculation circuit 870 corresponds to the shape calculation circuit 96 of the shape calculation system 90 shown in FIG. 2.

Detection light guided by the light guide member $LG_2$ is lost at the bend sensor $DP_1$. The loss quantity of the guided light varies in accordance with the direction of bend of the light guide member $LG_2$ and the quantity of the bend, as shown in FIG. 11A to FIG. 11C.

Figure 11A:
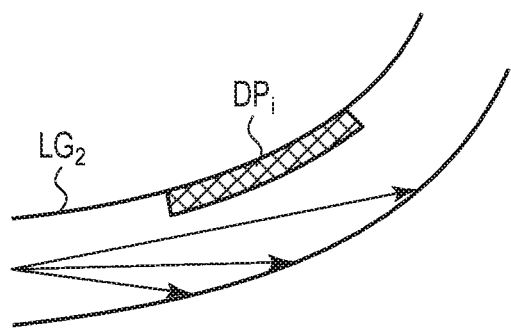
FIG. 11A is a view for describing the shape calculation system shown in FIG. 10, and schematically shows transmission of light when a light guide member is bent so that a bend sensor is located in the inside of bend of the light guide member.
Figure 11B:
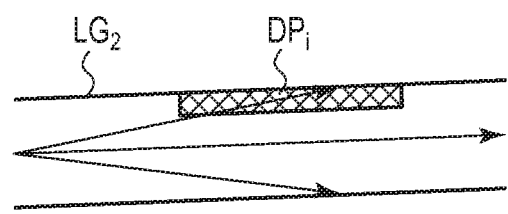
FIG. 11B is a view for describing the shape calculation system shown in FIG. 10, and schematically shows transmission of light when the light guide member is not bent.

For example, when the light guide member $LG_2$ is bent so that the bend sensor $DP_i$ is at the inside of the bend of the light guide member $LG_2$, as shown in FIG. 11A, the guided light loss quantity is less than when the light guide member $LG_2$ is not bent as shown in FIG. 11B. In addition, the guided light loss quantity becomes smaller in accordance with a bend quantity, i.e. a curvature, of the light guide member $LG_2$.

Figure 11C:
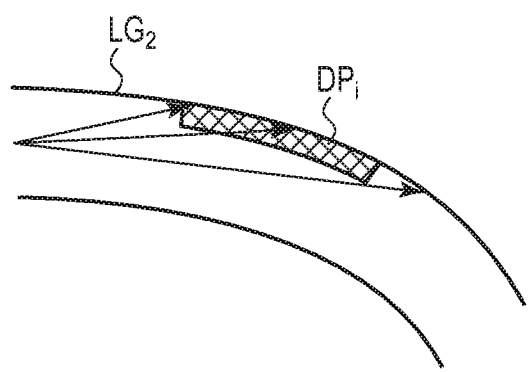
FIG. 11C is a view for describing the shape calculation system shown in FIG. 10, and schematically shows transmission of light when the light guide member is bent so that the bend sensor is located on the outside of bend of the light guide member.

Conversely, when the light guide member $LG_2$ is bent so that the bend sensor $DP_i$ is at the outside of the bend of the light guide member $LG_2$, as shown in FIG. 11C, the guided light loss quantity is greater than when the light guide member $LG_2$ is not bent as shown in FIG. 11B. In addition, the guided light loss quantity becomes greater in accordance with a bend quantity, i.e. a curvature, of the light guide member $LG_2$.

The variation of the guided light loss quantity is reflected on the quantity of detection light received by the light detector 830. Specifically, the variation of the guided light loss quantity is reflected on detection information from the light detector 830. Accordingly, monitoring the detection information from the light detector 830 allows recognizing the direction and quantity of the bend of the light guide member $LG_2$.

In FIG. 10, the light emitted from the light source 810 is guided by the light guide member $LG_1$ and enters the light branching element 850. The light branching element 850 divides the input light and outputs the divided light to two light guide members $LG_2$ and $LG_3$.

The light guided by the light guide member $LG_3$ is, for example, absorbed by the antireflection member 860 provided on an end portion of the light guide member $LG_3$.

The light guided by the light guide member $LG_2$ is reflected by the reflection member 840 provided on an end portion of the light guide member $LG_2$, and is then guided by the light guide member $LG_2$ and returned to the light branching element 850. While light is being guided by the light guide member $LG_2$, a wavelength component of the light, which corresponds to the bend sensor $DP_i$, is lost by the bend sensor $DP_i$.

The light branching element 850 divides the returned light, and outputs part of the light to the light guide member $LG_4$. The light output to the light guide member $LG_4$ is guided by the light guide member $LG_4$ and enters the light detector 830. The light received by the light detector 830 is light that has passed through the bend sensor $DP_i$, and the quantity of light varies depending on the curvature of the bend sensor $DP_i$.

Based on the detection information from the light detector 830, the shape calculation circuit 870 calculates the shape of the light guide member $LG_2$ of the fiber sensor 820.

The shape calculation circuit 870 includes a storage device 872, a light quantity calculation circuit 874, and a curvature calculation circuit 878.

The storage device 872 stores a light quantity calculation relationship representative of a relationship among the shape, wavelength, and light quantity for the bend sensors $DP_i$. The storage device 872 also stores various kinds of information necessary for calculation performed by the shape calculation circuit 870, such as information of positions of the bend sensors $DP_i$.

The light quantity calculation circuit 874 calculates light quantity information from the detection information from the light detector 830, and transmits the calculated light quantity information to the curvature calculation circuit 878.

The curvature calculation circuit 878 reads out the light quantity calculation relationship from the storage device 872, and calculates, based on the read-out light quantity calculation relationship, a light quantity calculation value representative of the relationship between a wavelength and a light quantity corresponding to each bend sensor $DP_i$. The curvature calculation circuit 878 further calculates the curvature of each of the bend sensors $DP_i$, based on the calculated light quantity calculation value, and the light quantity information supplied from the light quantity calculation circuit 874.

The shape calculation circuit 870 reads out the information of the position of each bend sensor $DP_i$ from the storage device 872, and calculates shape information of the light guide member $LG_2$, in which the bend sensors $DP_i$ are provided, based on the read-out information of the position, and the curvature of each bend sensor $DP_i$ calculated by the curvature calculation circuit 878. The shape calculation circuit 870 outputs the calculated shape information of the light guide member $LG_2$ as the information of the bend shape of the insertion section 24, in which the fiber sensor 820 including the light guide member $LG_2$ is assembled.

Accordingly, the shape calculation system 800 can recognize a three-dimensional position of various portions of the insertion section 24, with the three-dimensional position and direction of a specific location of the insertion section 24 being set as a reference. Specifically, the shape calculation system 800 can recognize the three-dimensional position of various portions of the insertion section 24, relative to a predetermined reference position, by detecting the three-dimensional position and direction of a specific location of the insertion section 24 relative to the predetermined reference position.

[Insertion Support Operation]

Next, an insertion support operation of the insertion section 24 in the flexible tube insertion apparatus 10 will be described. Hereinafter, the description will be given on the assumption that the endoscope 20 is a colonoscope and the tract of the observation target is the large intestine of a patient. In the stiffness control system 80, in the initial state, all stiffness changing devices 82 are controlled so as to be in the soft state. Thus, the soft tube 24c is in a state in which the soft tube 24c is most easily bent.

The insertion section 24 of the endoscope 20 is inserted from the anus into the large intestine. The insertion section 24 inserted in the large intestine is advanced, by the operator's pushing operation, from the anus to the rectum and further to the colon. The insertion section 24 advanced in the large intestine moves into the large intestine while the soft tube 24c is bending in accordance with the bend shape of the large intestine.

The image processing circuit of the imaging system 70 processes an image signal acquired by the imaging element 72 provided in the hard distal section 24a of the insertion section 24 of the endoscope 20, and causes the display 40 to display an optical image of the inner wall of the large intestine.

The insertion section 24 inserted in the large intestine often exhibits various loop shapes such as an α loop, a γ loop, and an N loop, in particular, in the sigmoid colon. When the insertion section 24 is further advanced deeper, the operator often advances the hard distal section 24a to a deep part of the descending colon, while forming a loop in the soft tube 24c in the sigmoid colon. When advancing the insertion section 24, partly enhancing the stiffness of the soft tube 24c improves the insertability of the insertion section 24, so that the insertion section 24 can be advanced with a weak pushing force quantity, and the load on the operator and the load on the patient are decreased.

FIG. 12 shows the insertion section 24 inserted in the large intestine 190. To be more specific, FIG. 12 shows the insertion section 24 in the state in which the hard distal section 24a passes through the sigmoid colon 194 and reaches the descending colon 196. As shown in FIG. 12, in the sigmoid colon 194, two bend portions 24ca and 24cb are normally formed in the soft tube 24c. The bend portion 24ca is a bend portion located on the distal side of the soft tube 24c, and the bend portion 24cb is a bend portion located on the proximal side of the soft tube 24c. Hereinafter, for the purpose of convenience, the bend portion 24ca is referred to as "distal bend portion 24ca", and the bend portion 24cb is referred to as "proximal bend portion 24cb", as needed. Normally, the directions of the bend portions 24ca and 24cb are different from each other. The soft tube 24c exhibits various loop shapes due to a difference in three-dimensional shape between the bend portions 24ca and 24cb.

The inventors have discovered, through various experiments and researches, that the three-dimensional positional relationship between the distal bend portion 24ca and proximal bend portion 24cb influences the relationship between the stiffness of the insertion section 24c and the advancement of the insertion section 24. The three-dimensional positional relationship between the distal bend portion 24ca and proximal bend portion 24cb can be discussed, for example, based on the relationship between the direction of the distal bend portion 24ca and the direction of the proximal bend portion 24cb in a three-dimensional space. The relationship between the direction of the distal bend portion 24ca and the direction of the proximal bend portion 24cb can also be discussed based on the crossing angle between an imaginary plane passing through the distal bend portion 24ca and an imaginary plane passing through the proximal bend portion 24cb.

Figure 13:
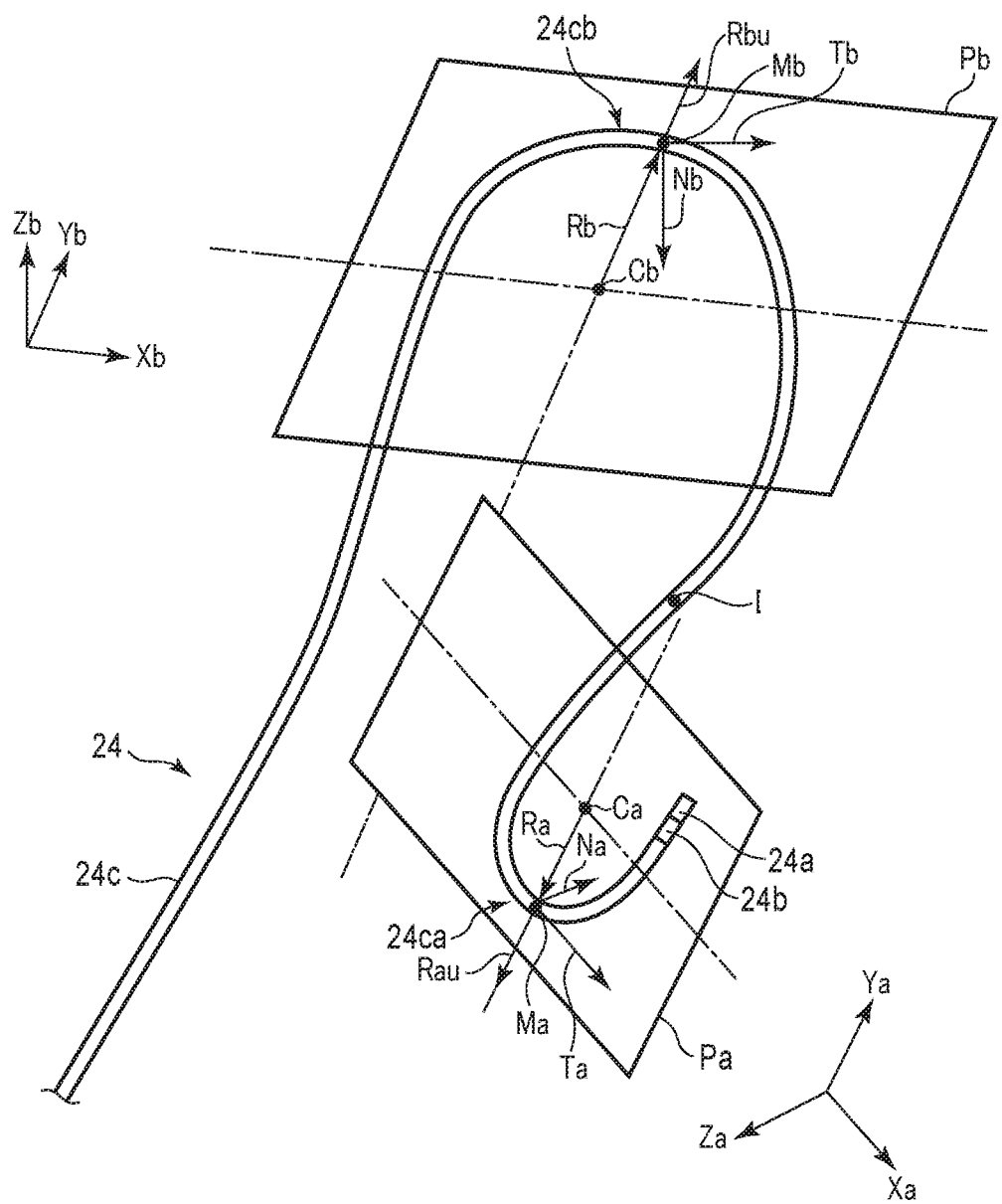
FIG. 13 shows an insertion section in which two bend portions are formed.

FIG. 13 shows the insertion section 24 in which two bend portions 24ca and 24cb are formed. FIG. 13 also shows imaginary planes Pa and Pb passing through the bend portions 24ca and 24cb, respectively. Hereinafter, for the purpose of convenience, the imaginary plane passing through the distal bend portion 24ca is referred to as "distal imaginary plane Pa" and the imaginary plane passing through the proximal bend portion 24cb is referred to as "proximal imaginary plane Pb", as needed. In FIG. 13, the distal imaginary plane Pa and the proximal imaginary plane Pb define an XaYaZa coordinate system and an XbYbZb coordinate system, respectively.

The bend portions 24ca and 24cb are, for example, portions in a range of the soft tube 24c in which the curvature exceeds a threshold. The bend portions 24ca and 24cb have curvature maximum points Ma and Mb, respectively. The curvature maximum points Ma and Mb are points on the center axis of the soft tube 24c where the curvatures take maximum values.

Here, for the purpose of convenience, radial vectors Ra and Rb, tangent vectors Ta and Tb, and normal vectors Na and Nb are defined as described below. The radial vector Ra, Rb is a vector from a curvature center Ca, Cb of the bend portion 24ca, 24cb toward the curvature maximum point Ma, Mb. Further, it is assumed that the unit vector of the radial vector Ra, Rb is a radial unit vector Rau, Rbu. The tangent vector Ta, Tb is a unit vector parallel to a tangent at the curvature maximum point Ma, Mb. The tangent vector Ta, Tb has the curvature maximum point Ma, Mb as a starting point. The tangent vector Ta, Tb has, at the curvature maximum point Ma, Mb, a direction from the proximal side toward the distal side of the insertion section 24. The normal vector Na, Nb is defined by an outer product between the radial unit vector Rau, Rbu and the tangent vector Ta, Tb.

The imaginary plane Pa, Pb is defined by a plane formed by the radial unit vector Rau, Rbu and the tangent vector Ta, Tb. The normal vector Na, Nb is parallel to a normal to the imaginary plane Pa, Pb. In addition, the normal vector Na, Nb has a direction corresponding to the direction of the bend portion 24ca, 24cb.

FIG. 14 is a perspective view of the distal imaginary plane Pa and proximal imaginary plane Pb. In addition, FIG. 15 is a side view of the distal imaginary plane Pa and proximal imaginary plane Pb. FIG. 14 and FIG. 15 show a crossing angle θ between the distal imaginary plane Pa and proximal imaginary plane Pb. The crossing angle θ is defined by an angle formed between the two normal vectors Na and Nb. The crossing angle θ has a value in a range of ±180 degrees, with one of the normal vectors Na and Nb being set as a reference. Hereinafter, the crossing angle θ is examined, with the normal vector Nb being set as the reference.

For example, in the shape of the insertion section 24 projected on an XbYb plane, if the two bend portions 24ca and 24cb are bent in opposite directions, the two normal vectors Na and Nb have opposite signs. Here, if simply expressed, the fact that the two bend portions 24ca and 24cb are bent in opposite directions corresponds to the fact that the shape of the insertion section 24 is a so-called S shape. In other words, the fact that the two bend portions 24ca and 24cb are bent in opposite directions corresponds to the fact that the curvature centers Ca and Cb of the bend portions 24ca and 24cb are located on opposite sides with reference to a tangent at a point on the center axis of the soft tube 24c between the two bend portions 24ca and 24cb, for example, with reference to a tangent at an inflection point I of the two bend portions 24ca and 24cb.

In this case, in the three-dimensional space, the crossing angle θ between the two imaginary planes Pa and Pb takes a value in −180 degrees<θ<−90 degrees, or 90 degrees<θ<180 degrees.

Conversely, in the shape of the insertion section 24 projected on the XbYb plane, if the two bend portions 24ca and 24cb are bent in the same direction, the two normal vectors Na and Nb have the same sign. Here, the fact that the two bend portions 24ca and 24cb are bent in the same direction corresponds to the fact that the curvature centers Ca and Cb of the bend portions 24ca and 24cb are located on the same side with reference to a tangent at a point on the center axis of the soft tube 24c between the two bend portions 24ca and 24cb, for example, with reference to a tangent at the inflection point I of the two bend portions 24ca and 24cb.

In this case, in the three-dimensional space, the crossing angle θ between the two imaginary planes Pa and Pb takes a value in −90 degrees<θ<90 degrees.

The loop shapes of the soft tube 24c are generally classified into three patterns. Hereinafter, for the purpose of convenience, the three patterns are referred to as "A pattern", "B pattern", and "C pattern".

Figure 16:
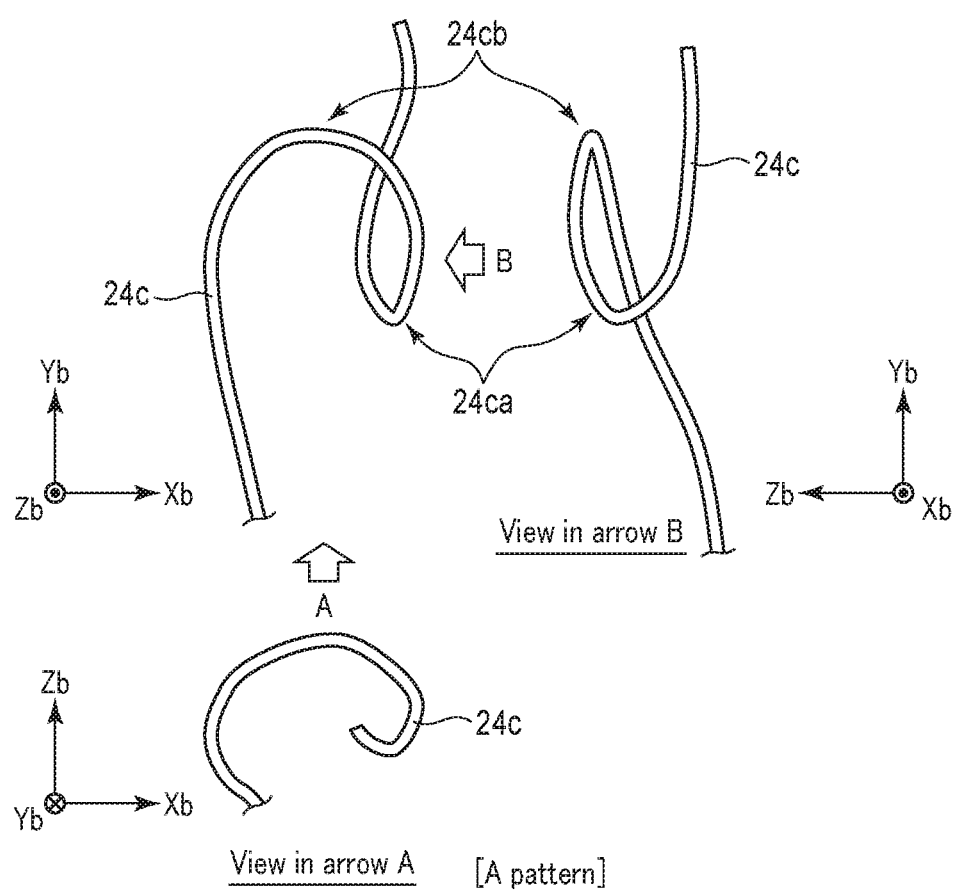
FIG. 16 shows a soft tube having a loop shape of an A pattern, which is one of three patterns of the loop shape of the soft tube, in an XbYbZb coordinate system determined by the proximal imaginary plane.

FIG. 16 shows the soft tube 24c having a loop shape of the A pattern, which is one of the three patterns of the loop shape of the soft tube 24c. The soft tube 24c is depicted with reference to an XbYbZb coordinate system determined by the proximal imaginary plane Pb. To be more specific, the soft tube 24c is depicted, with a coordinate plane determined by two coordinate axes of the XbYbZb coordinate system being set in parallel to the surface of the drawing sheet. The loop shape of the A pattern is a shape corresponding to a so-called a loop. In the soft tube 24c of the loop shape of the A pattern, the crossing angle θ between the two imaginary planes Pa and Pb is a value in −90 degrees<θ<90 degrees.

Figure 17:
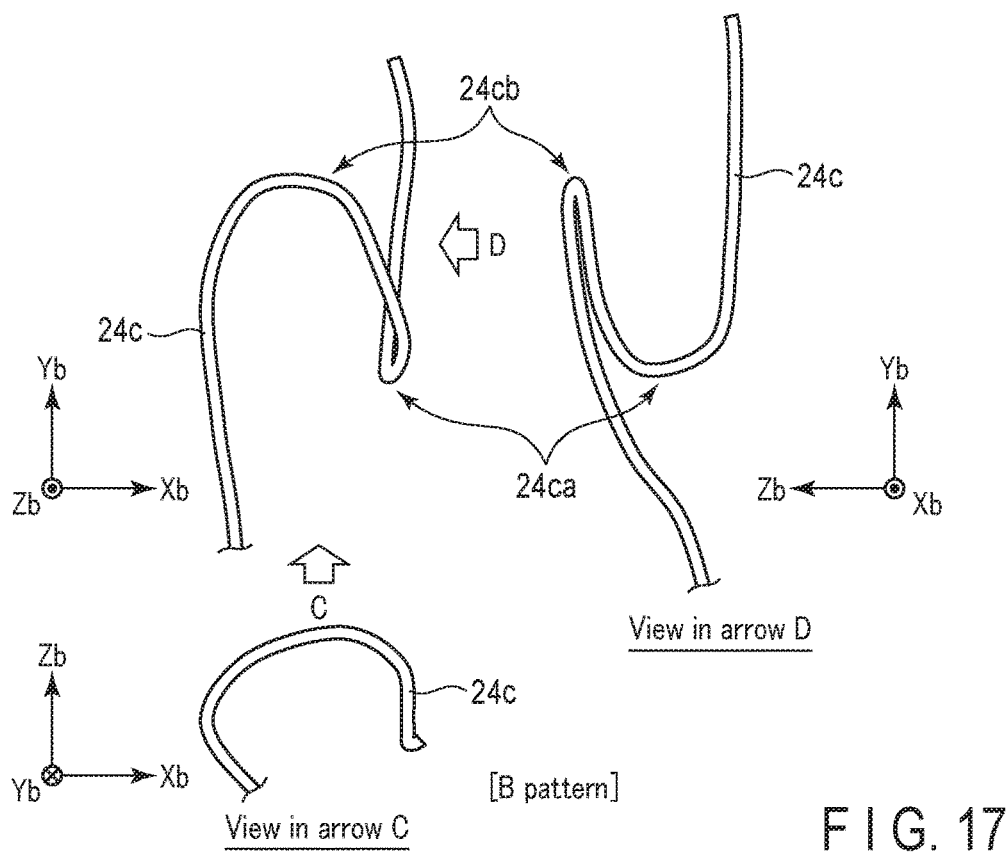
FIG. 17 shows a soft tube having a loop shape of a B pattern, which is another pattern of the loop shape of the soft tube, in the XbYbZb coordinate system determined by the proximal imaginary plane.

FIG. 17 shows the soft tube 24c having a loop shape of the B pattern, which is another pattern of the loop shape of the soft tube 24c. As in FIG. 16, the soft tube 24c is depicted with reference to the XbYbZb coordinate system. In the soft tube 24c of the loop shape of the B pattern, the crossing angle θ between the two imaginary planes Pa and Pb is a value of approximately −90 degrees or approximately 90 degrees.

Figure 18:
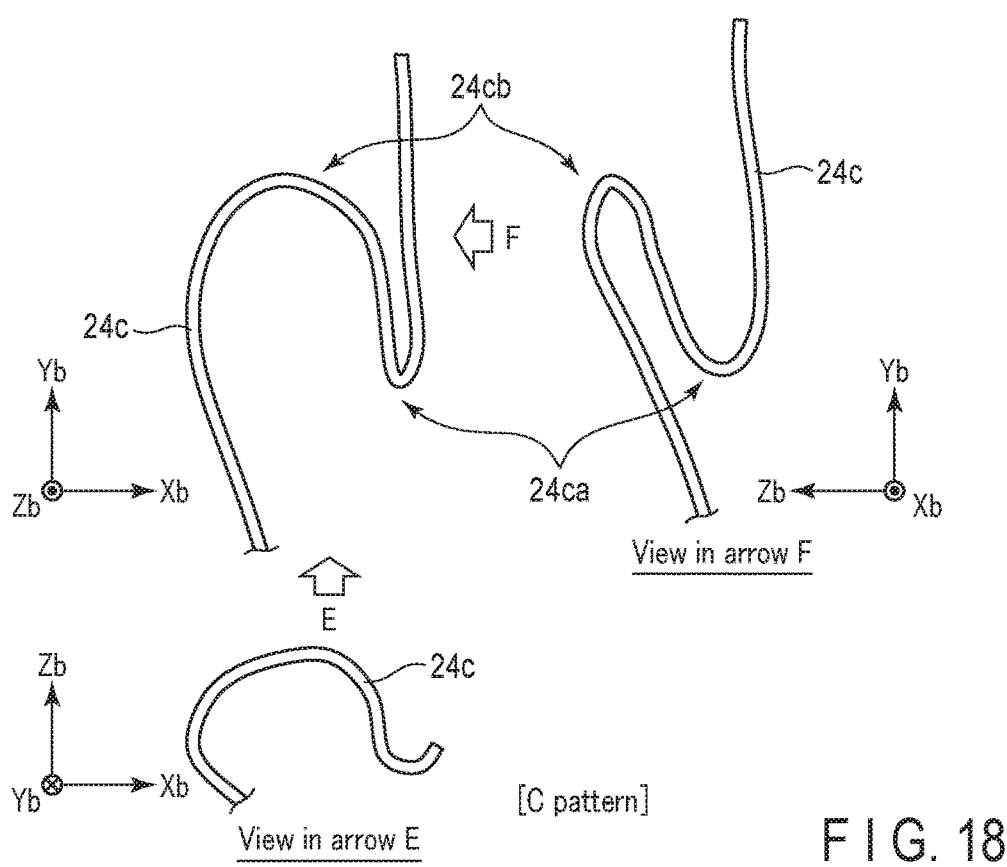
FIG. 18 shows a soft tube having a loop shape of a C pattern, which is the other pattern of the loop shape of the soft tube, in the XbYbZb coordinate system determined by the proximal imaginary plane.

FIG. 18 shows the soft tube 24c having a loop shape of the C pattern, which is the other pattern of the loop shape of the soft tube 24c. As in FIG. 16, the soft tube 24c is depicted with reference to the XbYbZb coordinate system. The loop shape of the C pattern is a shape corresponding to a so-called N loop. In the soft tube 24c of the loop shape of the C pattern, the crossing angle θ between the two imaginary planes Pa and Pb is a value in −180 degrees<θ<−90 degrees, or 90 degrees<θ<180 degrees.

Figure 19:
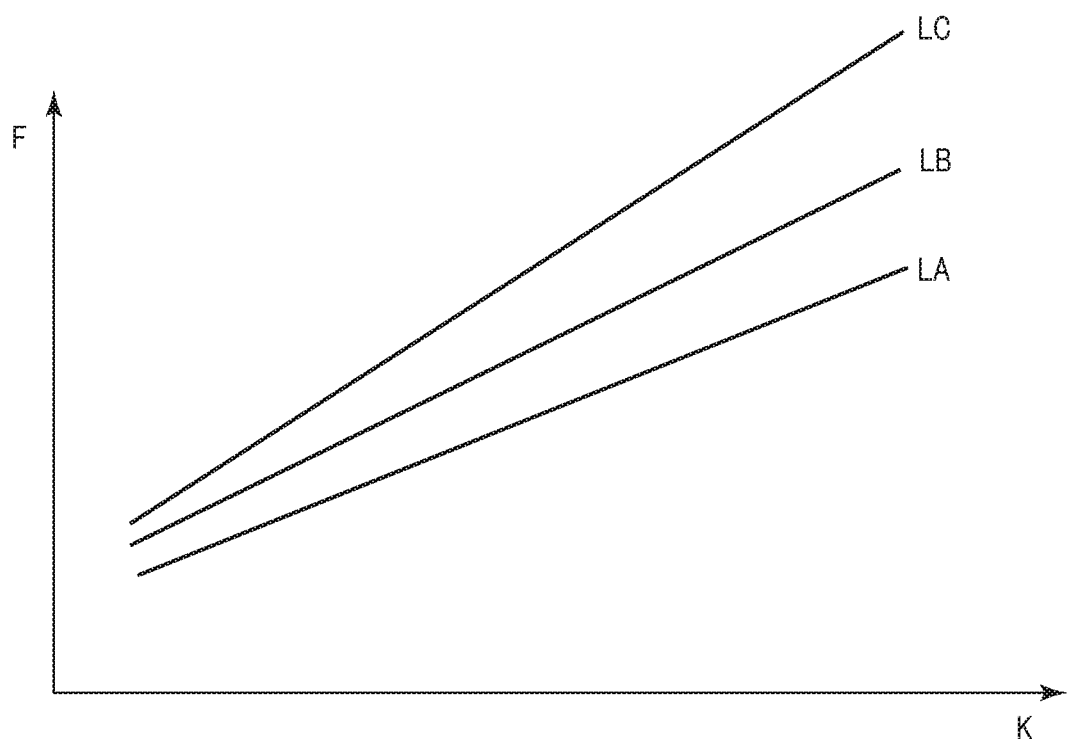
FIG. 19 is a graph showing a relationship between a stiffness K of the stiffness changing device and a force F with which a portion of the soft tube provided with the stiffness changing device tries to advance in association with an identical insertion operation on the proximal side.

The inventors discovered, through experiments, that even if a part of the insertion section 24 has an identical stiffness, a force to urge further advancement varies depending on the shape of the loop shape. FIG. 19 is a graph showing a relationship between a stiffness K of the stiffness changing device 82 and a force F with which a portion of the soft tube 24c provided with the stiffness changing device 82 is urged to further advance in association with an identical insertion operation on the proximal side. LA is indicative of the relation of the force F to the stiffness K in the insertion section 24 of a loop shape that is an example of the A pattern. LB is indicative of the relation of the force F to the stiffness K in the insertion section 24 of a loop shape of the B pattern. LC is indicative of the relation of the force F to the stiffness K in the insertion section 24 of a loop shape that is an example of the C pattern.

It is understood from FIG. 19 that, with respect to an identical stiffness, the force F to urge further advancement is greater in the insertion section 24 of the loop shape of the B pattern than in the insertion section 24 of the loop shape of the A pattern, and the force F to urge further advancement is greater in the insertion section 24 of the loop shape of the C pattern than in the insertion section 24 of the loop shape of the B pattern.

In other words, for the insertion section 24 of the loop shape of the C pattern, if the stiffness changing device 82 is controlled so as to have a stiffness value that provides a force F proper for the loop shape of the A pattern, the force F to urge further advancement may become excessive. This situation may apply an excessive load to the intestinal wall of the large intestine 190.

Accordingly, it is understood that, in order to optimize the force F to urge further advancement, it is important to control the stiffness K in accordance with the loop shape of the insertion section 24.

The flexible tube insertion apparatus 10 according to the present embodiment performs an insertion support operation of supporting the insertion of the insertion section 24 in accordance with the loop shape of the insertion section 24.

FIG. 20 shows a flowchart of a process in the insertion support operation of the insertion section 24 in the flexible tube insertion apparatus 10. The process of FIG. 20 is executed mainly by the bend detection circuit 110 and the positional relationship calculation circuit 140. The flowchart of FIG. 20 illustrates a process from immediately after the start of an insertion support operation function of the flexible tube insertion apparatus 10 to the stop of the insertion support operation function of the flexible tube insertion apparatus 10. The start and the stop of the insertion support operation function are executed by, for example, the switches 22e of the control section 22.

After the insertion support operation function of the flexible tube insertion apparatus 10 is started, the shape calculation system 90 starts monitoring the shape of the insertion section 24. In step S1, the shape calculation circuit 96 calculates the shape of the insertion section 24, and outputs the information of the shape of the insertion section 24. The calculation of the shape of the insertion section 24 by the shape calculation system 90 is continued until the insertion support operation function is stopped. The information of the shape of the insertion section 24 is displayed, for example, on the display 40.

In addition, the bend detection circuit 110 starts monitoring the formation of two bend portions in the soft tube 24c. In step S2, the bend detection circuit 110 detects the formation of two bend portions in the soft tube 24c.

The bend detection circuit 110 acquires the information of the shape of the insertion section 24 from the shape calculation circuit 96, and detects, based on the acquired information, the formation of two bend portions in the soft tube 24c. For example, the bend detection circuit 110 detects the formation of two bend portions by acquiring the information of the curvature of various portions of the soft tube 24c from the shape calculation circuit 96, comparing the curvature of various portions with the threshold for the bend portion detection, determining a range with a curvature exceeding the threshold to be a bend portion, and counting the number of portions that are determined to be bend portions. The bend detection circuit 110 outputs information, e.g. position information, of the two detected bend portions to the positional relationship calculation circuit 140. When the formation of two bend portions in the soft tube 24c is not detected, the process advances to step S5 of determining the stop of the insertion support operation function.

When the formation of two bend portions in the soft tube 24c is detected in step S2, the positional relationship calculation circuit 140 calculates, in step S3, the three-dimensional positional relationship of the two bend portions in response to the detection of the formation of two bend portions in the soft tube 24c. Hereinafter, it is assumed that the two bend portions are the two bend portions 24ca and 24cb shown in FIG. 13. As described above, the three-dimensional positional relationship is, for example, the crossing angle θ between the two imaginary planes Pa and Pb respectively passing through the two bend portions 24ca and 24cb. The positional relationship calculation circuit 140 further calculates a portion of the soft tube 24c that the stiffness is to be enhanced, and the magnitude of the stiffness that is provided to this portion.

FIG. 21 shows a configuration example of the positional relationship calculation circuit 140. As shown in FIG. 21, the positional relationship calculation circuit 140 includes an imaginary plane calculation circuit 142, a crossing angle calculation circuit 144, a stiffness-to-be-enhanced portion calculation circuit 146, and a storage device 148.

The imaginary plane calculation circuit 142, crossing angle calculation circuit 144, and stiffness-to-be-enhanced portion calculation circuit 146 are composed of combinations of processors and storage devices, for example. Alternatively, the imaginary plane calculation circuit 142, crossing angle calculation circuit 144, and stiffness-to-be-enhanced portion calculation circuit 146 may be composed of combinations of exclusive circuits and general-purpose circuits.

The imaginary plane calculation circuit 142 calculates the imaginary planes Pa and Pb, based on the information, e.g. the positional information, of the two bend portions 24ca and 24cb, the information being input from the bend detection circuit 110 to the positional relationship calculation circuit 140.

The crossing angle calculation circuit 144 calculates the crossing angle θ between the two imaginary planes Pa and Pb, based on the information of the two imaginary planes Pa and Pb calculated by the imaginary plane calculation circuit 142.

The stiffness-to-be-enhanced portion calculation circuit 146 calculates a portion of the soft tube 24c in which the stiffness is to be enhanced, based on the information, e.g. position information, of the two bend portions 24ca and 24cb, the information being input from the bend detection circuit 110 to the positional relationship calculation circuit 140. Hereinafter, the portion of the soft tube 24c in which the stiffness is to be enhanced is referred to simply as "stiffness-to-be-enhanced portion", for the purpose of convenience.

FIG. 22 is a graph showing a radius of curvature R of various portions of the insertion section 24 inserted in the large intestine 190. In FIG. 22, the ordinate axis represents the radius of curvature R and the abscissa axis represents a length from the distal end of the insertion section 24. As illustrated in FIG. 22, the radius of curvature R takes a minimum value at the curvature maximum point Ma, Mb of the bend portion 24ca, 24cb.

The stiffness-to-be-enhanced portion calculation circuit 146 calculates, as a stiffness-to-be-enhanced portion, at least a portion of the part of the bend portion 24ca, 24cb that is located on the distal side with respect to the curvature maximum point Ma, Mb. For example, the stiffness-to-be-enhanced portion calculation circuit 146 calculates, as a stiffness-to-be-enhanced portion, the part of the bend portion 24ca, 24cb that is located on the distal side with respect to the curvature maximum point Ma, Mb.

For example, the stiffness-to-be-enhanced portion calculation circuit 146 calculates the radii of curvature of various portions of the bend portions 24ca and 24cb, based on the information, e.g. the position information, of the two bend portions 24ca and 24cb. The stiffness-to-be-enhanced portion calculation circuit 146 compares the radii of curvature of the various portions of the bend portions 24ca and 24cb with a threshold Rth for stiffness-to-be-enhanced portion determination.

The threshold Rth is, for example, a value corresponding to the above-described threshold for the bend portion detection. The threshold Rth does not necessarily need to be the value corresponding to the threshold for the bend portion detection, and may be a value different from the value corresponding to the threshold for the bend portion detection.

As a result of the comparison, the stiffness-to-be-enhanced portion calculation circuit 146 calculates, as stiffness-to-be-enhanced portions, the parts of the bend portions 24ca and 24cd that correspond to length ranges La and Lb in which the radii of curvature are lower than the threshold Rth.

Here, although the example is described in which the stiffness-to-be-enhanced portion is calculated based on the radius of curvature of various portions of the bend portion 24ca, 24cb, the stiffness-to-be-enhanced portion may be calculated based on the curvature of various portions of the bend portion 24ca, 24cb, instead of the radius of curvature.

The stiffness-to-be-enhanced portion calculation circuit 146 further calculates the magnitude of stiffness that is provided to the stiffness-to-be-enhanced portion, based on the crossing angle θ between the two imaginary planes Pa and Pb calculated by the crossing angle calculation circuit 144. The magnitude of stiffness that is provided to the stiffness-to-be-enhanced portion is a control target value of the stiffness of the stiffness changing device 82 that is located in the stiffness-to-be-enhanced portion.

FIG. 23 is a graph showing a relationship between the magnitude of the crossing angle θ (i.e. the absolute value of θ) of the two imaginary planes Pa and Pb and a control target value J of the stiffness changing device 82. In FIG. 23, a straight line L1 indicates an example of a relational expression between the magnitude of the crossing angle θ and the control target value J. In addition, a straight line L2 indicates an example of a relational expression between the magnitude of the crossing angle θ and the control target value J that provides the maximum effect.

The stiffness-to-be-enhanced portion calculation circuit 146 calculates the control target value of the stiffness of the stiffness changing device 82 located in the stiffness-to-be-enhanced portion, based on the magnitude of the crossing angle θ of the two imaginary planes Pa and Pb, for example, in accordance with the straight line L1 of FIG. 23.

The storage device 148 stores the information, e.g. position information, of the stiffness-to-be-enhanced portion, and the control target value of the stiffness changing device 82 located in the stiffness-to-be-enhanced portion, the information and the control target value being calculated by the stiffness-to-be-enhanced portion calculation circuit 146.

In step S4, the stiffness control system 80 controls the stiffness of the stiffness-to-be-enhanced portion, based on the information stored in the storage device 148 in the positional relationship calculation circuit 140. Specifically, the stiffness control circuit 86 reads out the information of the stiffness-to-be-enhanced portion and the information of the control target value from the storage device 148 in the positional relationship calculation circuit 140, and changes the stiffness of the stiffness changing device 82 corresponding to the stiffness-to-be-enhanced portion to the control target value, based on the read-out information of the stiffness-to-be-enhanced portion and the read-out information of the control target value.

If the formation of two bend portions is not detected in step S2, it is determined in step S5 whether the stop of the insertion support operation function of the flexible tube insertion apparatus 10 is instructed or not. This determination is executed by, for example, the insertion control apparatus 30. The determination of the instruction to stop the insertion support operation function is executed, for example, based on the operation of the switches 22e of the control section 22. When it is determined in step S5 that the stop of the insertion support operation function of the flexible tube insertion apparatus 10 is not instructed, the process returns to step S1. On the other hand, when it is determined in step S5 that the stop of the insertion support operation function of the flexible tube insertion apparatus 10 is instructed, the insertion control apparatus 30 stops the insertion support operation function of the flexible tube insertion apparatus 10.

As is clear from the above description, in the flexible tube insertion apparatus 10, when the formation of two bend portions in the soft tube 24c is detected by the bend detection circuit 110, the stiffness of a portion of the bend portion 24ca, 24cb, for example, the stiffness of at least a portion of the part of the 24ca, 24cb that is located on the distal side with respect to the curvature maximum point Ma, Mb, is controlled by the stiffness control system 80. Thus, the insertability of the insertion section 24, in which a loop is formed, can be enhanced.

[Modification]

In the present modification, instead of calculating the crossing angle θ of the imaginary planes Pa and Pb, based on the shape of the soft tube 24c, the three-dimensional positional relationship between the two bend portions 24ca and 24cb is calculated based on the three-dimensional position information of various portions of the soft tube 24c.

Figure 24:
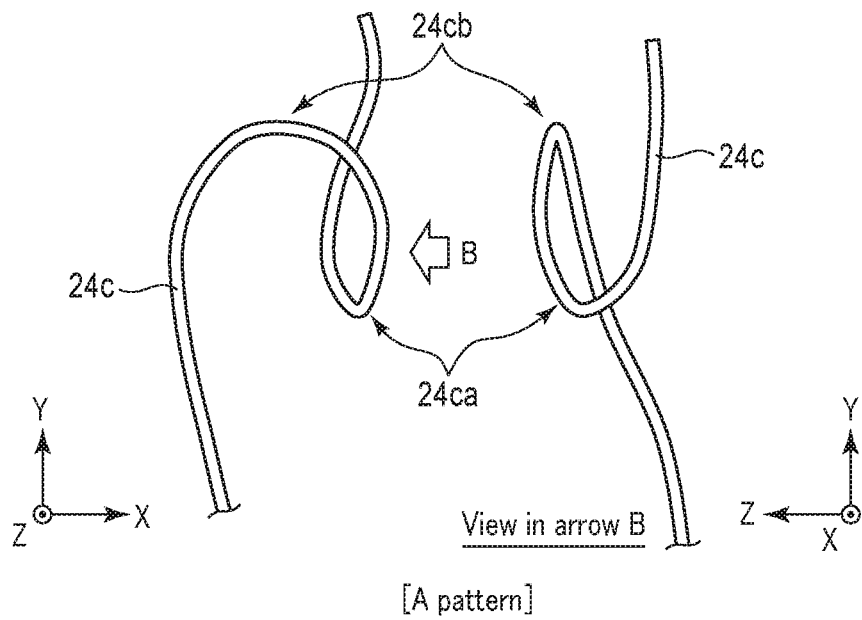
FIG. 24 shows the A pattern of the loop shape that the insertion section exhibits, in an XYZ coordinate system determined by an antenna.

FIG. 24 shows the soft tube 24c of the loop shape of the A pattern, which is one of the three patterns of the loop shape of the soft tube 24c. The soft tube 24c is depicted with reference to an XYZ coordinate system determined by the antenna 730. To be more specific, the soft tube 24c is depicted, with a coordinate plane determined by two coordinate axes of the XYZ coordinate system being set in parallel to the surface of the drawing sheet. The loop shape of the A pattern is a shape corresponding to a so-called a loop. In the loop shape of the A pattern, on the XY plane, an end portion on the distal side of the distal bend portion 24ca is located in the inside of the loop defined by the proximal bend portion 24cb.

Figure 25:
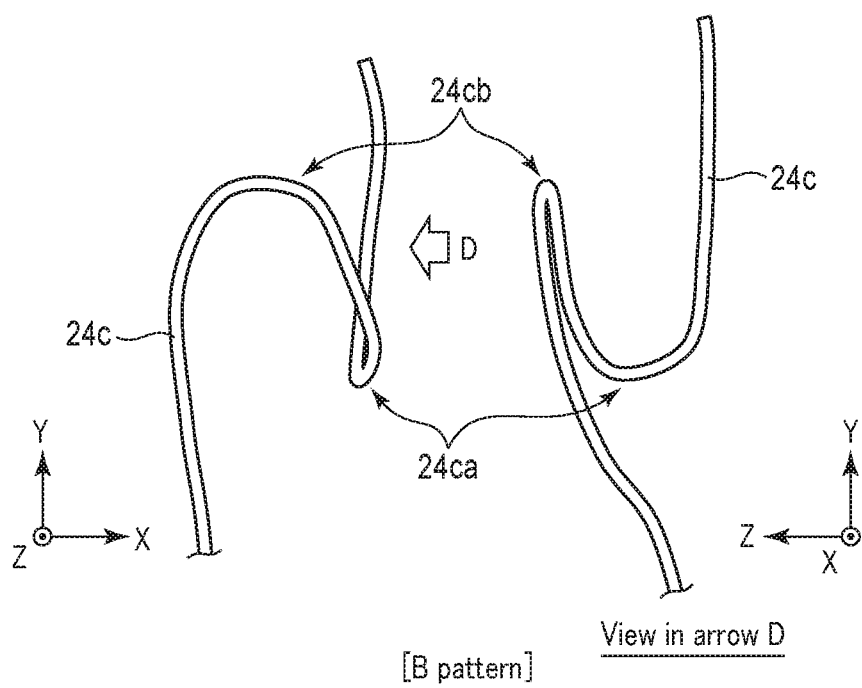
FIG. 25 shows the B pattern of the loop shape that the insertion section exhibits, in the XYZ coordinate system determined by the antenna.

FIG. 25 shows the soft tube 24c of the loop shape of the B pattern, which is another pattern of the loop shape of the soft tube 24c. The soft tube 24c is depicted with reference to the XYZ coordinate system, as in FIG. 24. In the loop shape of the B pattern, on the XY plane, an end portion on the distal side of the distal bend portion 24ca substantially overlaps the loop defined by the proximal bend portion 24cb.

Figure 26:
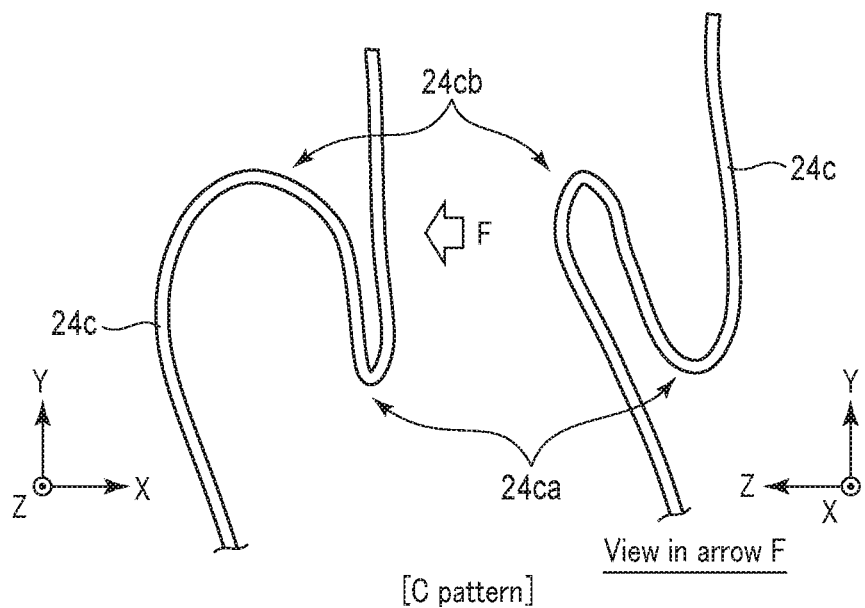
FIG. 26 shows the C pattern of the loop shape that the insertion section exhibits, in the XYZ coordinate system determined by the antenna.

FIG. 26 shows the soft tube 24c of the loop shape of the C pattern, which is the other pattern of the loop shape of the soft tube 24c. The soft tube 24c is depicted with reference to the XYZ coordinate system, as in FIG. 24. In the loop shape of the C pattern, on the XY plane, an end portion on the distal side of the distal bend portion 24ca is located on the outside of the loop defined by the proximal bend portion 24cb.

The positional relationship calculation circuit 140 acquires, from the shape calculation circuit 96, the three-dimensional position information of various portions of the soft tube 24c in the XYZ coordinate system, i.e. the three-dimensional position information of magnetic coils, and analyzes the pattern of the loop shape of the soft tube 24c, based on the acquired information. The positional relationship calculation circuit 140 further analyzes the degree of the loop of the soft tube 24c. Based on the analyzed pattern of the loop shape of the soft tube 24c, the positional relationship calculation circuit 140 calculates the control target value of the stiffness of the stiffness changing device 82 located in the stiffness-to-be-enhanced portion.

The degree of the loop of the soft tube 24c is the transverse width of the loop, for example, in the loop shape of the A pattern. For example, in the loop shape of the A pattern, the degree of the loop is the width of the loop, i.e. the degree of overlapping of the bend portions 24ca and 24cb. In addition, in the loop shape of the C pattern, the degree of the loop of the soft tube 24c is the degree of separation of the bend portions 24ca and 24cb. In other words, the degree of the loop of the soft tube 24c is the positional relationship between the proximal end of the distal bend portion 24ca and the distal end of the proximal bend portion 24cb.

Figure 27:
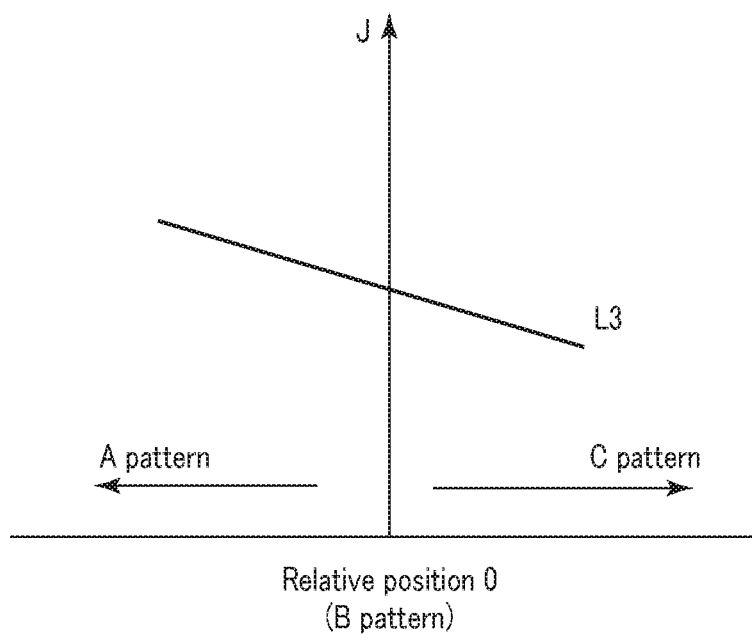
FIG. 27 is a graph showing a relationship between the pattern of the loop shape of the soft tube, and the control target value of the stiffness changing device that is located at a stiffness-to-be-enhanced portion.

FIG. 27 is a graph showing a relationship between the pattern of the loop shape of the soft tube 24c, and the control target value of the stiffness changing device 82 that is located in the stiffness-to-be-enhanced portion. The positional relationship calculation circuit 140 calculates the control target value J of the stiffness of the stiffness changing device 82 located in the stiffness-to-be-enhanced portion, in accordance with a straight line L3.

The present invention is not limited to the above-described embodiments. In practice, various modifications can be made without departing from the spirit of the invention. The embodiments can be properly combined and implemented as much as possible and, in this case, combined advantageous effects can be obtained. Further, the embodiments include inventions of various stages, and various inventions can be extracted by proper combinations of disclosed constituent elements.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
   a flexible tube to be inserted into a tract of a target;
   one or more shape sensors disposed in the flexible tube, the one or more shape sensors being configured to acquire shape information of the flexible tube;
   a processor comprising hardware, the processor being configured to:
     calculate a shape of the flexible tube based on an input of the shape information from the one or more shape sensors;
     detect formation of a first bend portion and a second bend portion in the flexible tube, based on the calculated shape of the flexible tube, the second bend portion being located on a proximal side of the flexible tube with respect to the first bend portion;
     calculate a crossing angle between a first imaginary plane passing through the first bend portion and a second imaginary plane passing through the second bend portion, the first bend portion and the second bend portion being different from each other in direction, the first imaginary plane being defined by a plane spanned by a first radial unit vector extending from a curvature center of the first bend portion toward a first curvature maximum point of the first bend portion and a first tangent vector serving as a unit vector parallel to a tangent at the first curvature maximum point, the second imaginary plane being defined by a plane spanned by a second radial unit vector extending from a curvature center of the second bend portion toward a second curvature maximum point of the second bend portion and a second tangent vector serving as a unit vector parallel to a tangent at the second curvature maximum point;
     calculate, based on the calculated crossing angle, a first position and first magnitude for controlling a first stiffness of the first bend portion and a second position and a second magnitude for controlling a second stiffness of the second bend portion; and
     control a stiffness of the flexible tube, based on the calculated first position, second position, first magnitude and second magnitude.

2. The flexible tube insertion apparatus according to claim 1, wherein the processor is configured to enhance the stiffness of the flexible tube to the first stiffness when the crossing angle is a first crossing angle, and configured to enhance the stiffness of the flexible tube to the second stiffness that is higher than the first stiffness, when the crossing angle is a second crossing angle having an absolute value that is less than an absolute value of the first crossing angle.

3. The flexible tube insertion apparatus according to claim 1, wherein the processor is configured to control a stiffness of a distal portion of the first bend portion in the flexible tube.

4. The flexible tube insertion apparatus according to claim 1, wherein the processor is configured to control a stiffness of a distal portion of the second bend portion in the flexible tube.

5. The flexible tube insertion apparatus according to claim 1, wherein the processor is configured to control a stiffness of a distal portion of the first bend portion in the flexible tube, and a stiffness of a distal portion of the second bend portion in the flexible tube.

6. The flexible tube insertion apparatus according to claim 2, wherein the absolute value of the first crossing angle is a value in 90 degrees to 180 degrees, and the absolute value of the second crossing angle is a value in 0 degrees to 90 degrees.

7. The flexible tube insertion apparatus according to claim 3, wherein the distal portion is a portion located on a distal side with respect to a part of the first bend portion where a curvature takes a maximum value.

8. The flexible tube insertion apparatus according to claim 1, wherein the processor is further configured to calculate the first imaginary plane and the second imaginary plane.

9. The flexible tube insertion apparatus according to claim 1, wherein
   the shape sensor includes magnetic coils that are configured to generate magnetic fields, the magnetic coils being provided on the flexible tube by being arranged along a longitudinal axis of the flexible tube,
   the one or more shape sensors include an antenna configured to receive the magnetic fields generated by the magnetic coils, the antenna being fixed on an outside of the target,
   the processor is configured to calculate, based on information of the magnetic fields received by the antenna, positions of the magnetic coils in a coordinate space determined based on the antenna, and configured to calculate the shape of the entirety of the flexible tube, based on the positions of the magnetic coils, and
   the processor is configured to calculate the first position of the first bend portion and the second position of the second bend portion, based on information of the shape of the entirety of the flexible tube, and configured to calculate the crossing angle, based on the first position of the first bend portion and the second position of the second bend portion.

10. The flexible tube insertion apparatus according to claim 1, wherein
    the one or more shape sensors include bend sensors arranged along a longitudinal axis of the flexible tube, each bend sensor being configured to detect a bend of a portion of the flexible tube on which the bend sensor is provided,
    the processor is configured to calculate, based on information of the bend detected by the bend sensors, curvatures of the various portions of the flexible tube, and configured to calculate the shape of the entirety of the flexible tube, based on the curvatures, and
    the processor is configured to calculate the first position of the first bend portion and the second position of the second bend portion, based on information of the shape of the entirety of the flexible tube, and configured to calculate the crossing angle, based on the first position of the first bend portion and the second position of the second bend portion.

11. The flexible tube insertion apparatus according to claim 1, further comprising stiffness changing devices and a stiffness controller configured to independently control the stiffness changing devices, the stiffness changing devices being provided on the flexible tube by being arranged along a longitudinal axis of the flexible tube, and each stiffness changing device being configured to change a stiffness of a portion of the flexible tube on which the stiffness changing device is provided.

12. An insertion control apparatus comprising:
a processor comprising hardware, the processor being configured to:
calculate a shape of a flexible tube to be inserted into a tract of a target based on an input of shape information from one or more shape sensors disposed in the flexible tube configured to acquire the shape information of the flexible tube;
detect formation of a first bend portion and a second bend portion in the flexible tube, based on the calculated shape of the flexible tube, the second bend portion being located on a proximal side of the flexible tube with respect to the first bend portion;
a crossing angle between a first imaginary plane passing through the first bend portion and a second imaginary plane passing through the second bend portion, the first bend portion and the second bend portion being different from each other in direction, the first imaginary plane being defined by a plane spanned by a first radial unit vector extending from a curvature center of the first bend portion toward a first curvature maximum point of the first bend portion and a first tangent vector serving as a unit vector parallel to a tangent at the first curvature maximum point, the second imaginary plane being defined by a plane spanned by a second radial unit vector extending from a curvature center of the second bend portion toward a second curvature maximum point of the second bend portion and a second tangent vector serving as a unit vector parallel to a tangent at the second curvature maximum point; and
calculate, based on the calculated crossing angle, a first position and first magnitude for controlling a first stiffness of the first bend portion and a second position and a second magnitude for controlling a second stiffness of the second bend portion; and
control a stiffness of the flexible tube, based on the calculated first position, second position, first magnitude and second magnitude.

* * * * *